US012685677B2

(12) United States Patent
Jang et al.

(10) Patent No.: US 12,685,677 B2
(45) Date of Patent: Jul. 21, 2026

(54) ABSORBENT ARTICLE WITH WAISTBAND

(71) Applicant: Kimberly-Clark Worldwide, Inc.,
Neenah, WI (US)

(72) Inventors: KyungSik Jang, Worcester Park (GB);
Alexey Markin, Stupino (RU);
JaeYoung Yoo, Reigate (GB); **Marta
Embid**, Reigate (GB)

(73) Assignee: Kimberly-Clark Worlwide, Inc.,
Neenah, WI (US)

( * ) Notice: Subject to any disclaimer, the term of this
patent is extended or adjusted under 35
U.S.C. 154(b) by 367 days.

(21) Appl. No.: 18/251,990

(22) PCT Filed: Dec. 21, 2020

(86) PCT No.: PCT/US2020/066358
§ 371 (c)(1),
(2) Date: May 5, 2023

(87) PCT Pub. No.: WO2022/139787
PCT Pub. Date: Jun. 30, 2022

(65) Prior Publication Data
US 2024/0009041 A1      Jan. 11, 2024

(51) Int. Cl.
*A61F 13/49*          (2006.01)
*A61F 13/15*          (2006.01)

(52) U.S. Cl.
CPC .. *A61F 13/49012* (2013.01); *A61F 13/15699*
(2013.01)

(58) Field of Classification Search
CPC .......... A61F 13/49011; A61F 13/49009; A61F
13/49007; A61F 13/49012; A61F
13/49019; A61F 2013/49025; A61F
2013/49038
See application file for complete search history.

(56) References Cited

U.S. PATENT DOCUMENTS 5,026,364 A      6/1991   Robertson
5,827,259 A  *  10/1998   Laux ................. A61F 13/49017
604/385.29
(Continued)

FOREIGN PATENT DOCUMENTS

CN        204468451 U      7/2015
CN        204863695 U     12/2015
(Continued)

OTHER PUBLICATIONS newbusi.com, "Application of non-woven fabrics on diapers and
their technical development trends", Apr. 18, 2019, https://www.
newbusi.com/news_show-id-14.html.

*Primary Examiner* — Catharine L Anderson
*Assistant Examiner* — Seth Han
(74) *Attorney, Agent, or Firm* — KIMBERLY-CLARK
WORLDWIDE, INC.

(57)          ABSTRACT

Absorbent articles comprising elastic waist members and
methods of manufactured are disclosed. In an embodiment,
an absorbent article may comprise a chassis including an
absorbent body and a body facing surface. The article may
further comprise a first adhesive disposed on the body facing
surface of the chassis and an elasticated waist member
coupled to the body facing surface of the chassis by the first
adhesive. The article may still further comprise a second
adhesive disposed on the elasticated waist member and a
waist region covering material coupled to the elasticated
waist member by the second adhesive.

10 Claims, 17 Drawing Sheets

(56) References Cited

U.S. PATENT DOCUMENTS

| | | | |
|---|---|---|---|
| 6,142,985 A * | 11/2000 | Feist ................. | A61F 13/49009 |
| | | | 604/385.28 |
| 6,595,976 B2 | 7/2003 | Jitoe et al. | |
| 10,722,407 B2 * | 7/2020 | Jones ...................... | A61F 13/53 |
| 2011/0146900 A1 | 6/2011 | Ruman | |
| 2017/0231835 A1 * | 8/2017 | Barnes ................. | A61F 13/495 |
| | | | 604/385.19 |
| 2017/0239106 A1 * | 8/2017 | Jones ............... | A61F 13/49011 |
| 2020/0085643 A1 | 3/2020 | Raycheck et al. | |

FOREIGN PATENT DOCUMENTS

| | | | |
|---|---|---|---|
| CN | 107920934 A | 4/2018 | |
| CN | 111031978 A | 4/2020 | |
| CN | 210962675 U | 7/2020 | |
| EP | 3318234 A1 | 5/2018 | |
| WO | 2004060204 A2 | 7/2004 | |
| WO | 2019131276 A1 | 7/2019 | |
| WO | 2019193906 A1 | 10/2019 | |

* cited by examiner

ABSORBENT ARTICLE WITH WAISTBAND

TECHNICAL FIELD

The present disclosure relates to absorbent articles. More particularly, the present disclosure relates to absorbent articles and waistbands.

BACKGROUND OF THE DISCLOSURE

A primary function of personal care absorbent articles is to absorb and retain body exudates such as urine, fecal material, blood, and menses with additional desired attributes including low leakage of the exudates from the absorbent article and a dry feel to the wearer of the absorbent article. By preventing leakage of the exudates from the absorbent article, the absorbent article intends to prevent the body exudates from soiling or contaminating a wearer's or caregiver's clothing or other articles, such as bedding, that can come in contact with the wearer.

One common mode of failure is for exudates to leak out of the rear waist region or the front waist region of an absorbent article. As one example, fecal material that is not absorbed or contained by the absorbent article can move past the gaps between the absorbent article and the wearer's skin in the rear waist region and soil or contaminate the wearer's skin and clothing near their back. This may be more common of an occurrence for semi-solid fecal material, such as low viscosity fecal material, which can be prevalent with younger children. Such exudates can move around on the bodyside liner of an absorbent article under the influence of gravity, motion, and pressure by the wearer of the absorbent article. In such a circumstance, not only does the wearer's absorbent article need to be changed, but the wearer's clothing and/or bedding often also needs to be changed, resulting in additional work, expense, and stress for the caregiver.

Attempts have been made in the past to mitigate or prevent such leaking, especially on the bodyside liner or near the rear waist region to solve the problems described above. One example is by providing a waist elastic member to ensure a secure fit of the article around a wearer. However, there is a further desire for improved waist elastic members to better provide for containment or mitigation of leaks as well as comfort.

SUMMARY OF THE DISCLOSURE

In one embodiment, an absorbent article including a front waist region including a front waist edge, a rear waist region including a rear waist edge, a crotch region disposed between the front waist region and the rear waist region, a longitudinal axis extending in a longitudinal direction and a lateral axis extending in a lateral direction may comprise a chassis including an absorbent body, the chassis including a body facing surface, a first adhesive disposed on the body facing surface of the chassis, an elasticated waist member coupled to the body facing surface of the chassis by the first adhesive, a second adhesive disposed on the elasticated waist member, and a waist region covering material coupled to the elasticated waist member by the second adhesive.

In another embodiment, an absorbent article including a front waist region including a front waist edge, a rear waist region including a rear waist edge, a crotch region disposed between the front waist region and the rear waist region, a longitudinal axis extending in a longitudinal direction and a lateral axis extending in a lateral direction may comprise a chassis including an absorbent body, the chassis including a body facing surface, a first adhesive disposed on the body facing surface of the chassis in the rear waist region, an elasticated waist member coupled to the body facing surface of the chassis in the rear waist region by the first adhesive, a first waist region covering material coupled to the body facing surface of the chassis and disposed entirely in the rear waist region, the first waist region covering material covering at least a portion of the elasticated waist member and having a lateral top edge and a lateral bottom edge, the lateral top edge being disposed closer to the rear waist edge than the lateral bottom edge, and a second waist region covering material coupled to the body facing surface of the chassis and disposed entirely in the front waist region and having a lateral top edge and a lateral bottom edge, the lateral top edge being disposed closer to the crotch region than the lateral bottom edge, the first waist region covering material and the second waist region covering material being formed of a same material. The lateral top edge of the first waist region covering material may be disposed at approximately the same longitudinal position as the rear waist edge such that the lateral top edge and the rear waist edge overlap in a vertical direction perpendicular to the longitudinal direction and the lateral direction, and the lateral bottom edge of the second waist region covering material may be disposed at approximately the same longitudinal position as the front waist edge such that the lateral bottom edge and the front waist edge overlap in the vertical.

In yet another embodiment, a method of forming absorbent articles may comprise moving a chassis web in a machine direction, the chassis web comprising an outer cover, an absorbent body, and a chassis web body facing surface, applying a first adhesive to the chassis web body facing surface, the first adhesive defining a first adhesive region, coupling an elasticated waist member to the chassis web with the first adhesive, applying a second adhesive to the elasticated waist member, coupling a waist region covering material to the elasticated waist member with the second adhesive, and severing the chassis web to form an individual absorbent article, the severing step comprises cutting through a portion of the chassis web comprising the first adhesive and the waist region covering material but not the elasticated waist member.

BRIEF DESCRIPTION OF DRAWINGS

A full and enabling disclosure thereof, directed to one of ordinary skill in the art, is set forth more particularly in the remainder of the specification, which makes reference to the appended figures in which.

3

Figure 2:
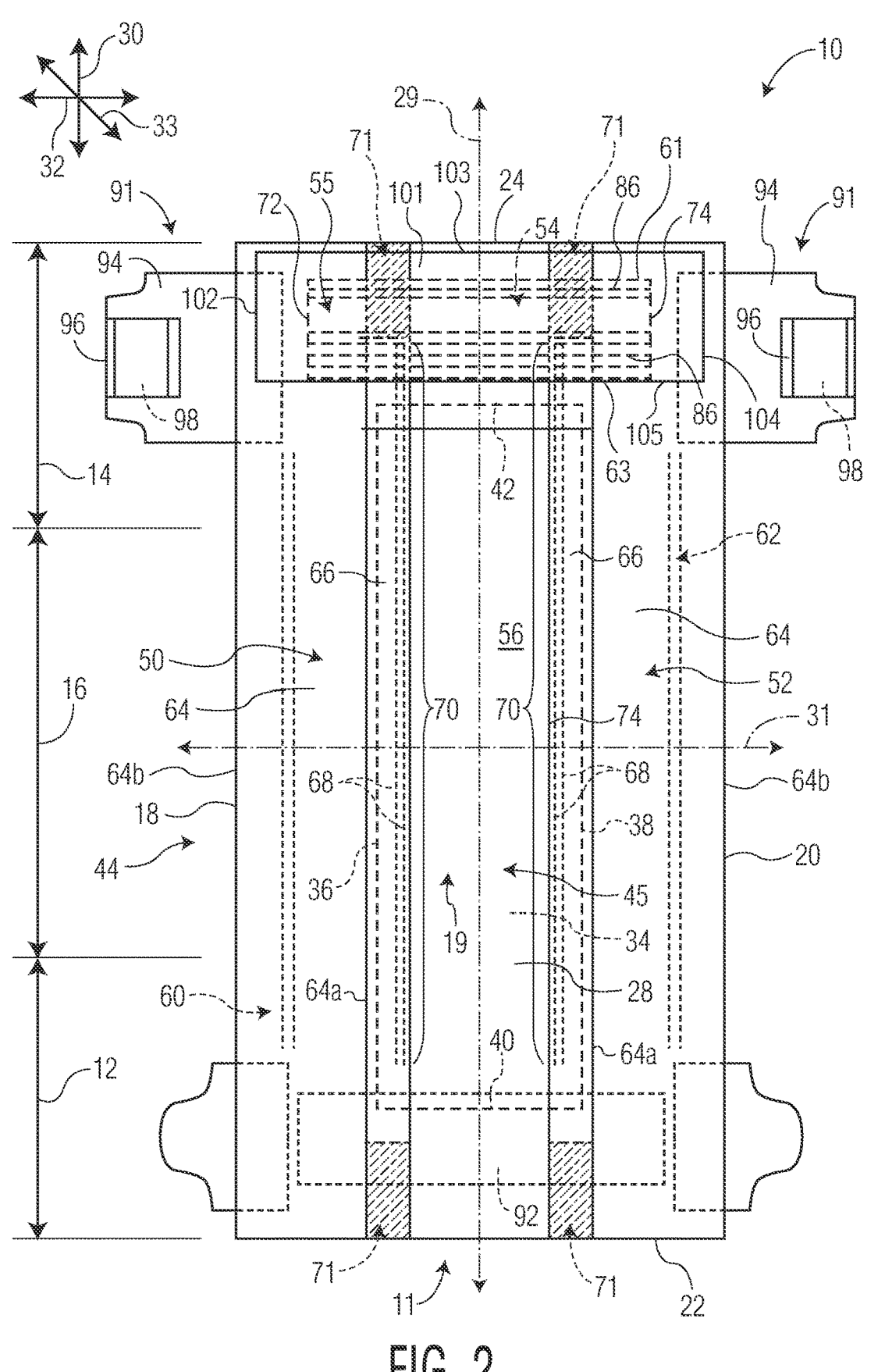
FIG. 2 is a top plan view of the absorbent article of FIG. 1 in a stretched, laid flat, unfastened condition.
Figure 4A:
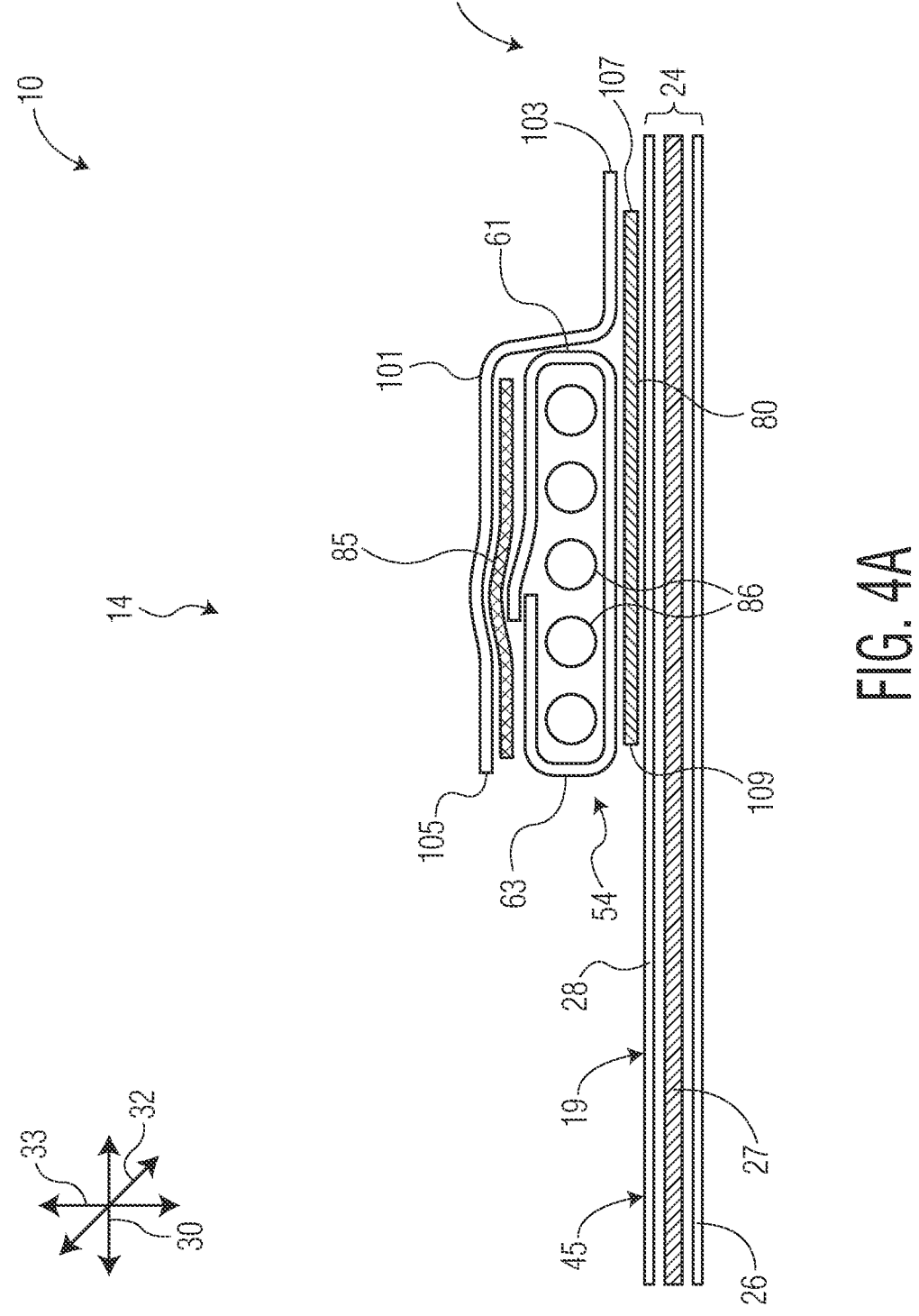
FIG. 4A is a cross-sectional view taken of an embodiment of the article of FIG. 2, taken long line 4-4, with the absorbent article being in a relaxed configuration.
Figure 4B:
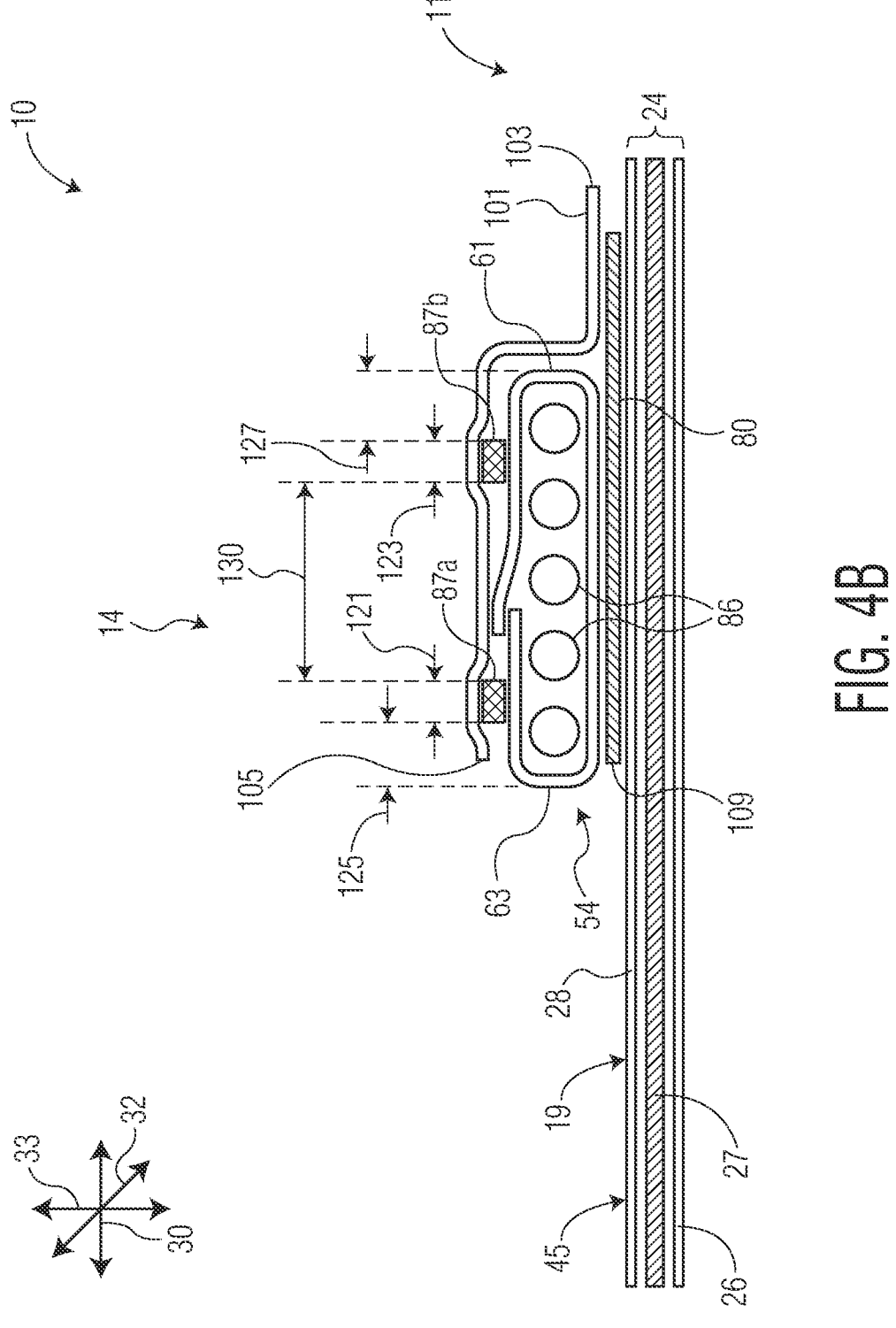

FIG. 4B is a cross-sectional view taken of an additional embodiment of the article of FIG. 2, taken long line 4-4, with the absorbent article being in a relaxed configuration.

Figure 1:
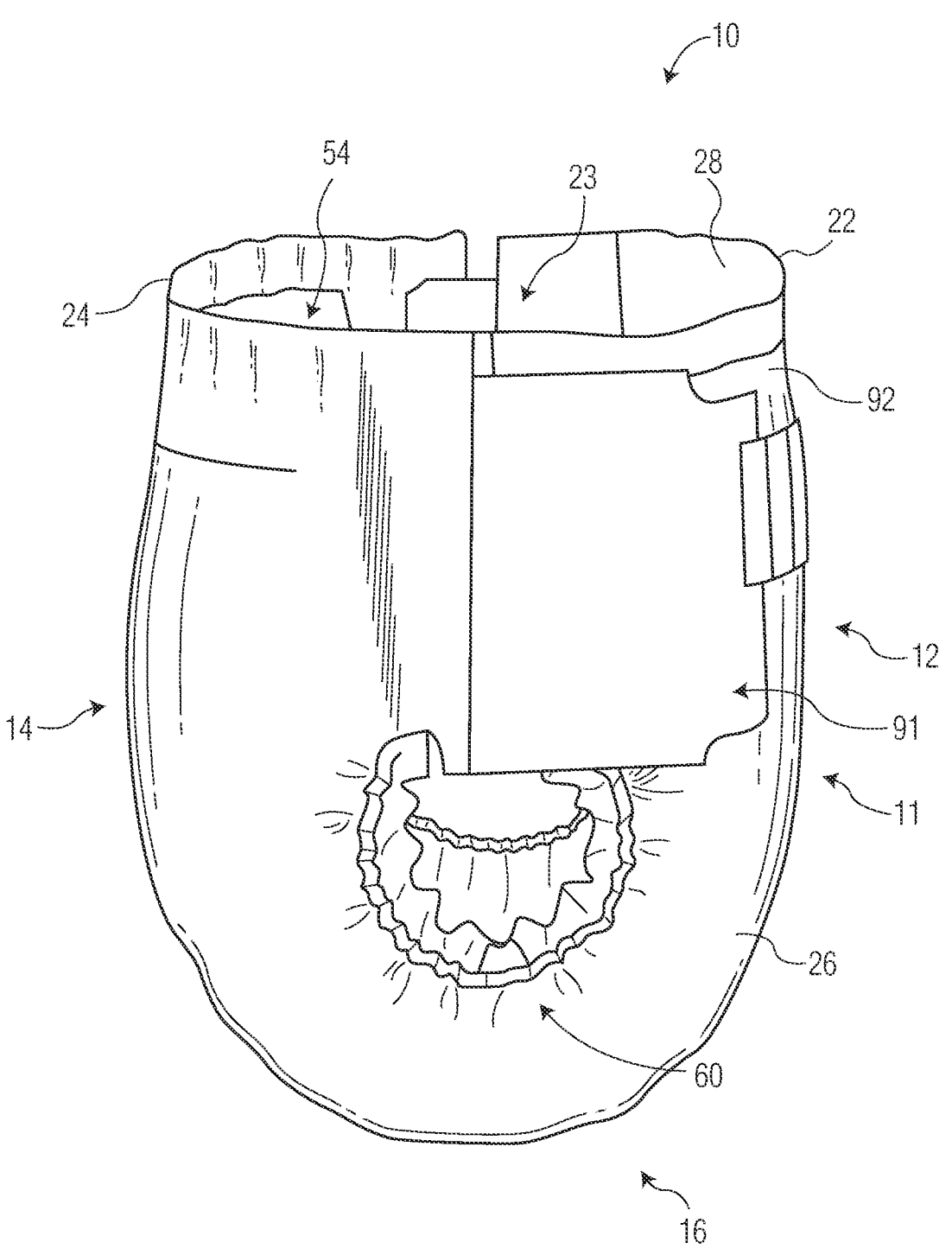
FIG. 1 is side perspective view of an exemplary embodiment of an absorbent article, such as a diaper, in a fastened condition.
Figure 5:
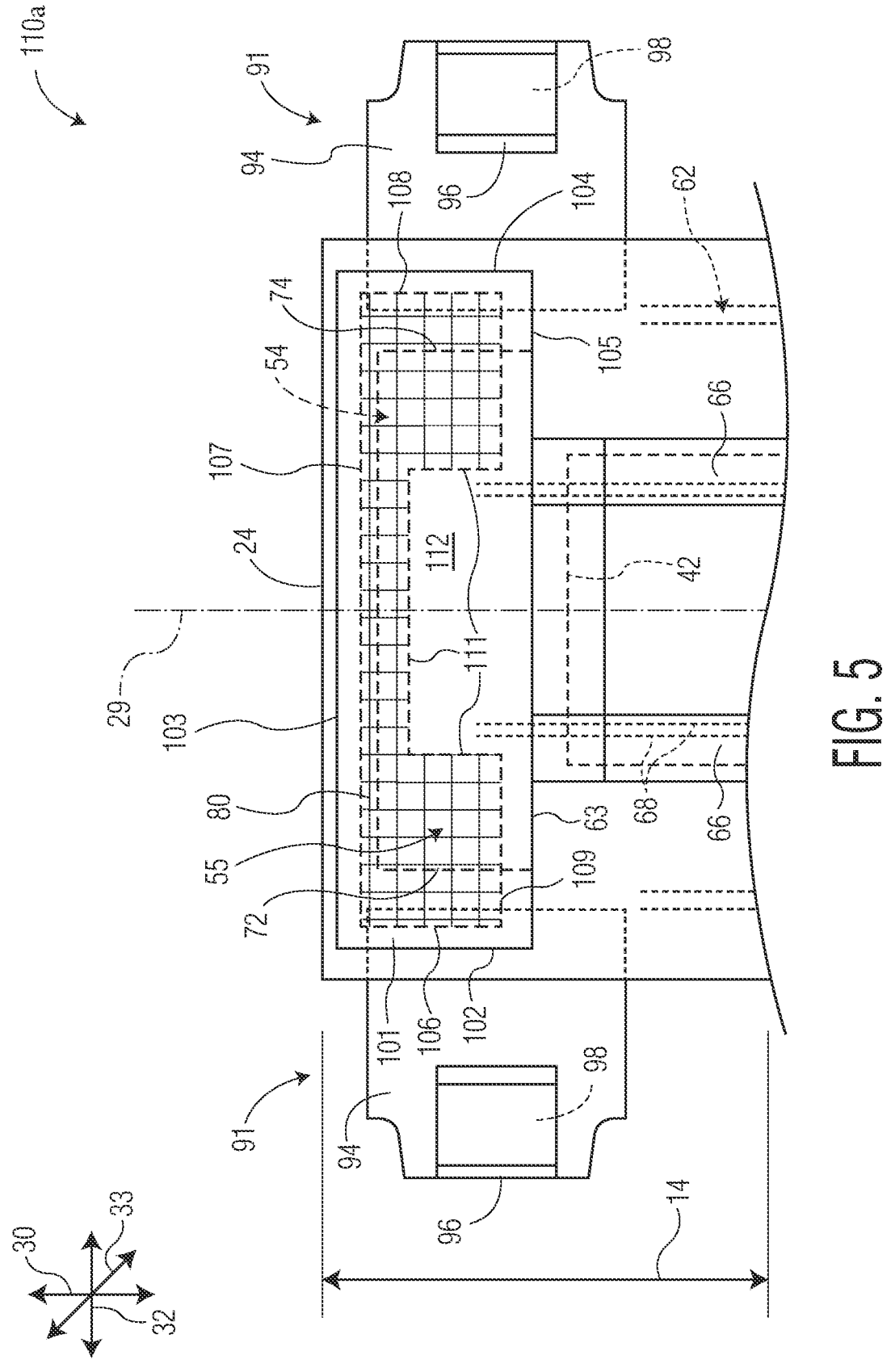

FIG. 5 is a close-up of a further embodiment of the rear waist region of the article of FIG. 1, with components removed to more clearly illustrate features according to aspects of the present disclosure.

Figure 6:
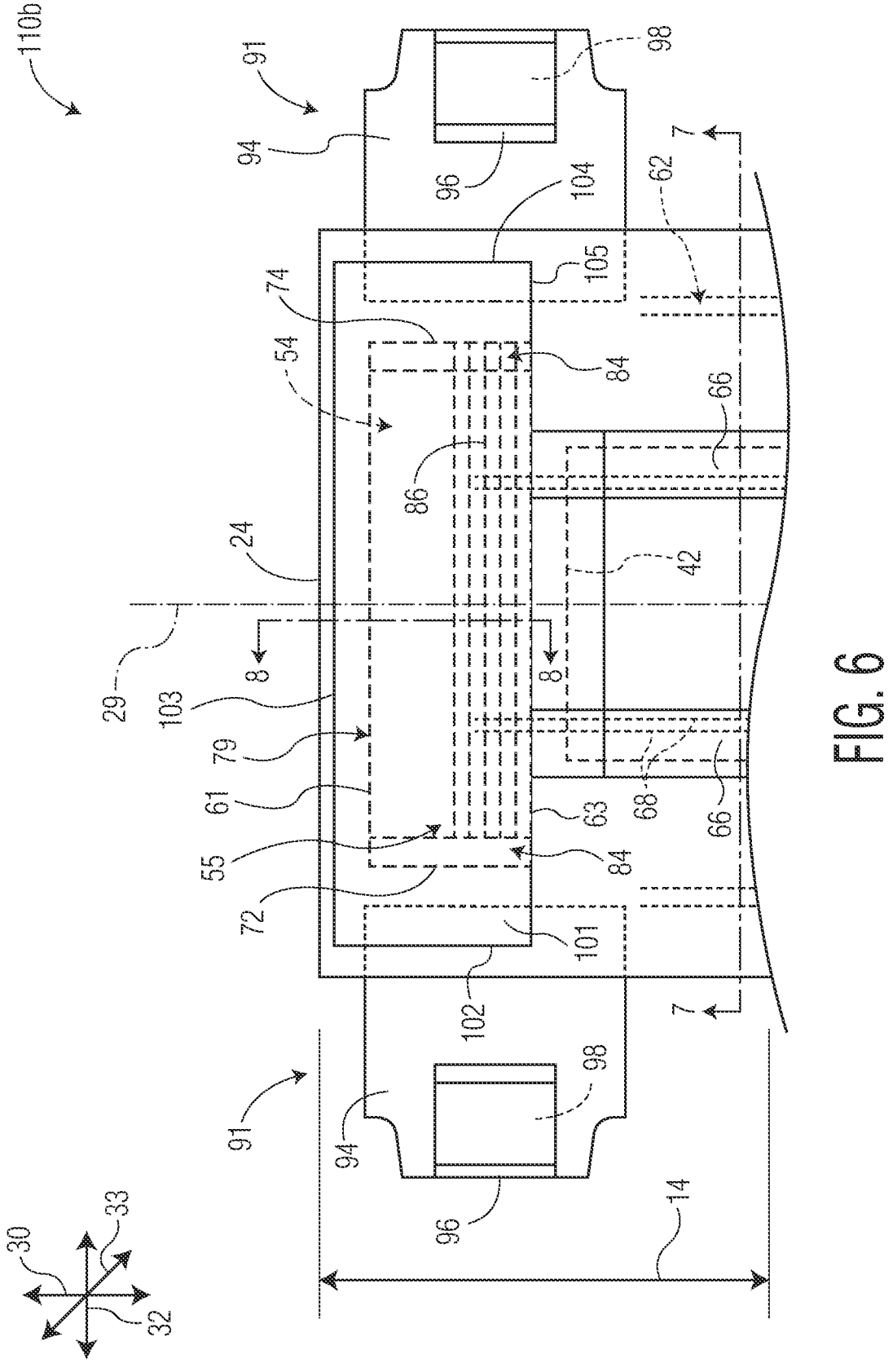

FIG. 6 is a close-up of a still further embodiment of the rear waist region of the article of FIG. 1, with components removed to more clearly illustrate features according to aspects of the present disclosure.

Figure 7:
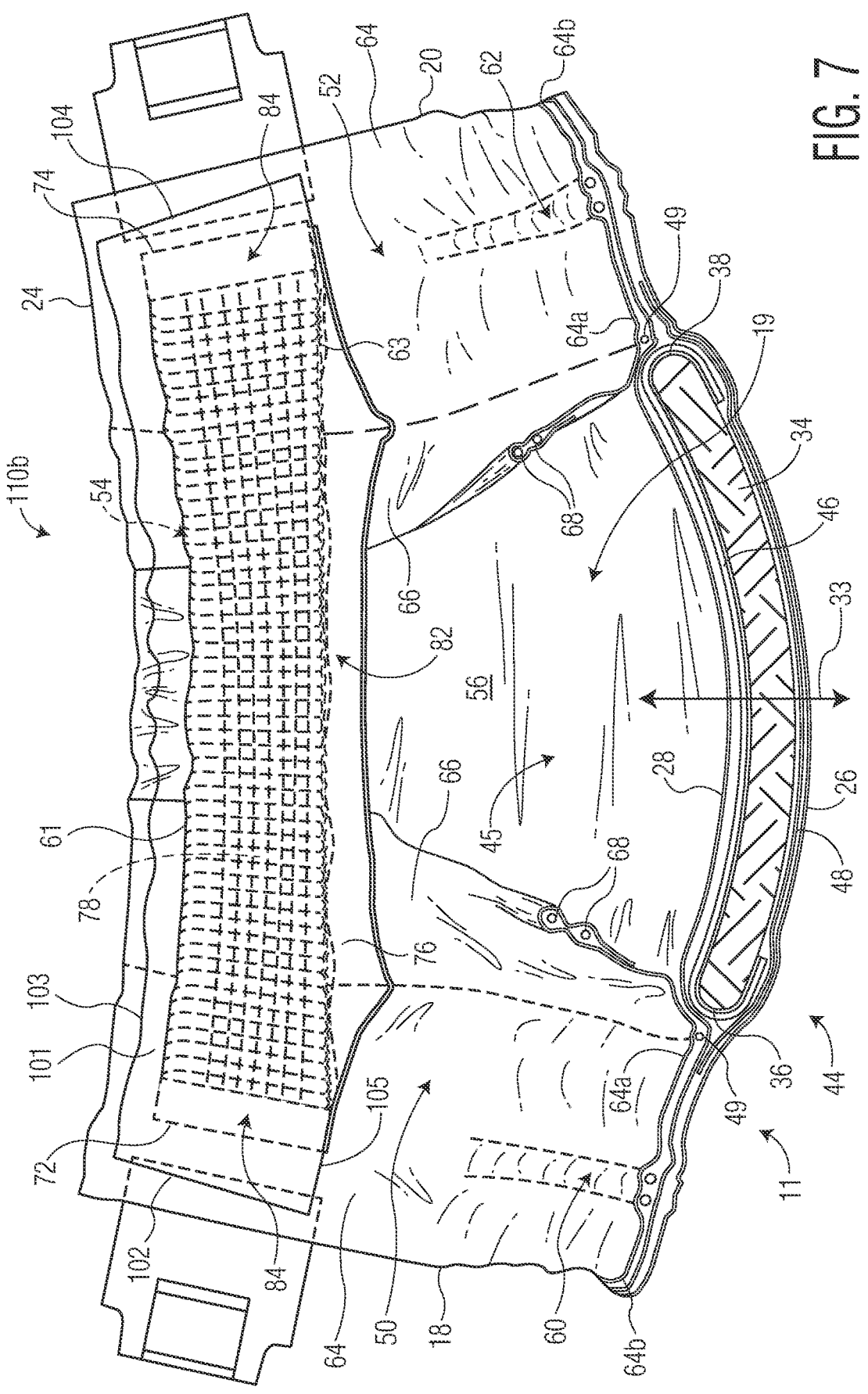

FIG. 7 is a front perspective cross-section view of the article of FIG. 6 taken along line 7-7, showing the article in a relaxed configuration.

Figure 8:
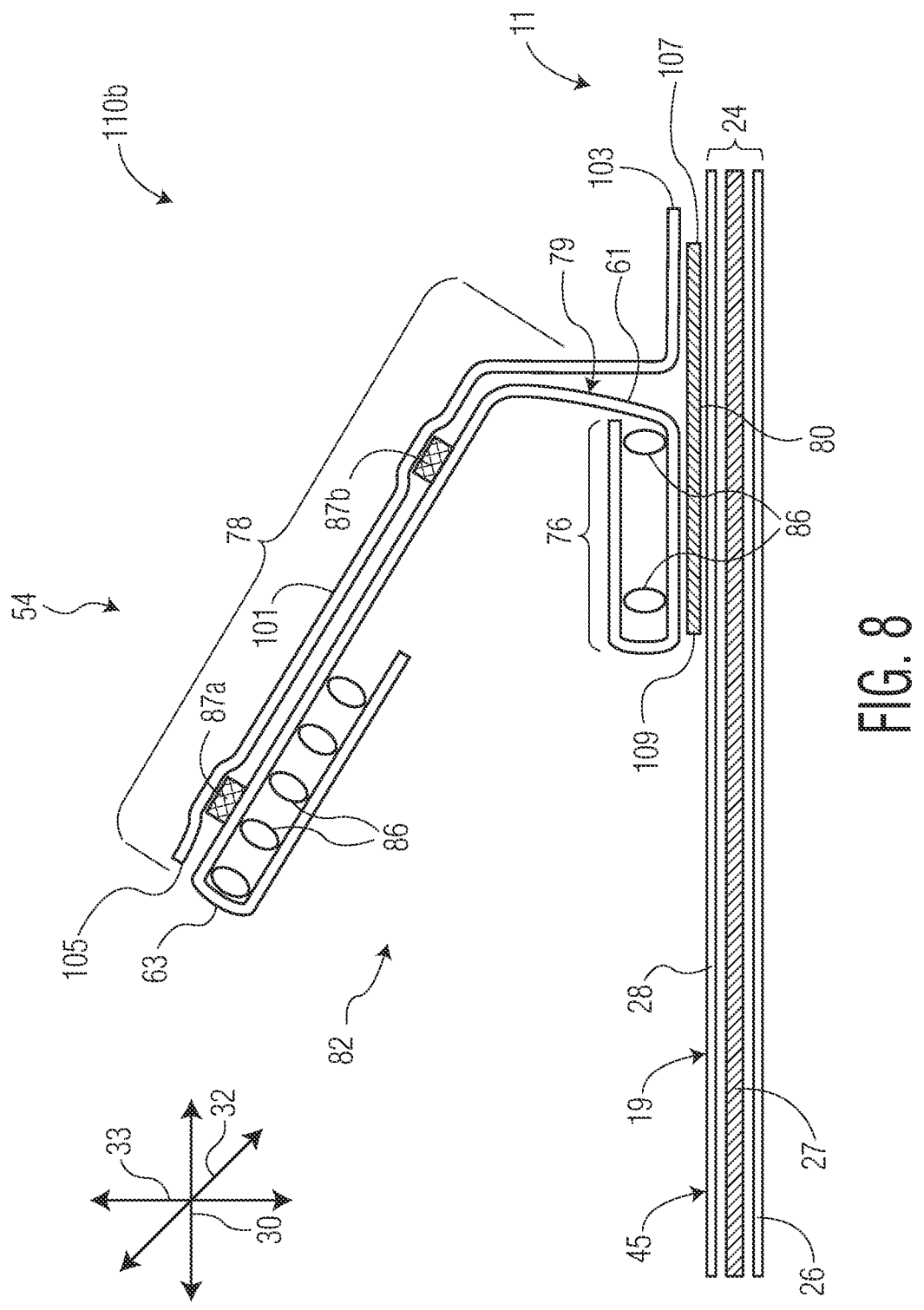

FIG. 8 is a side cross-section view of the article of FIG. 6 taken along line 8-8, showing the article in a relaxed configuration.

Figure 9:
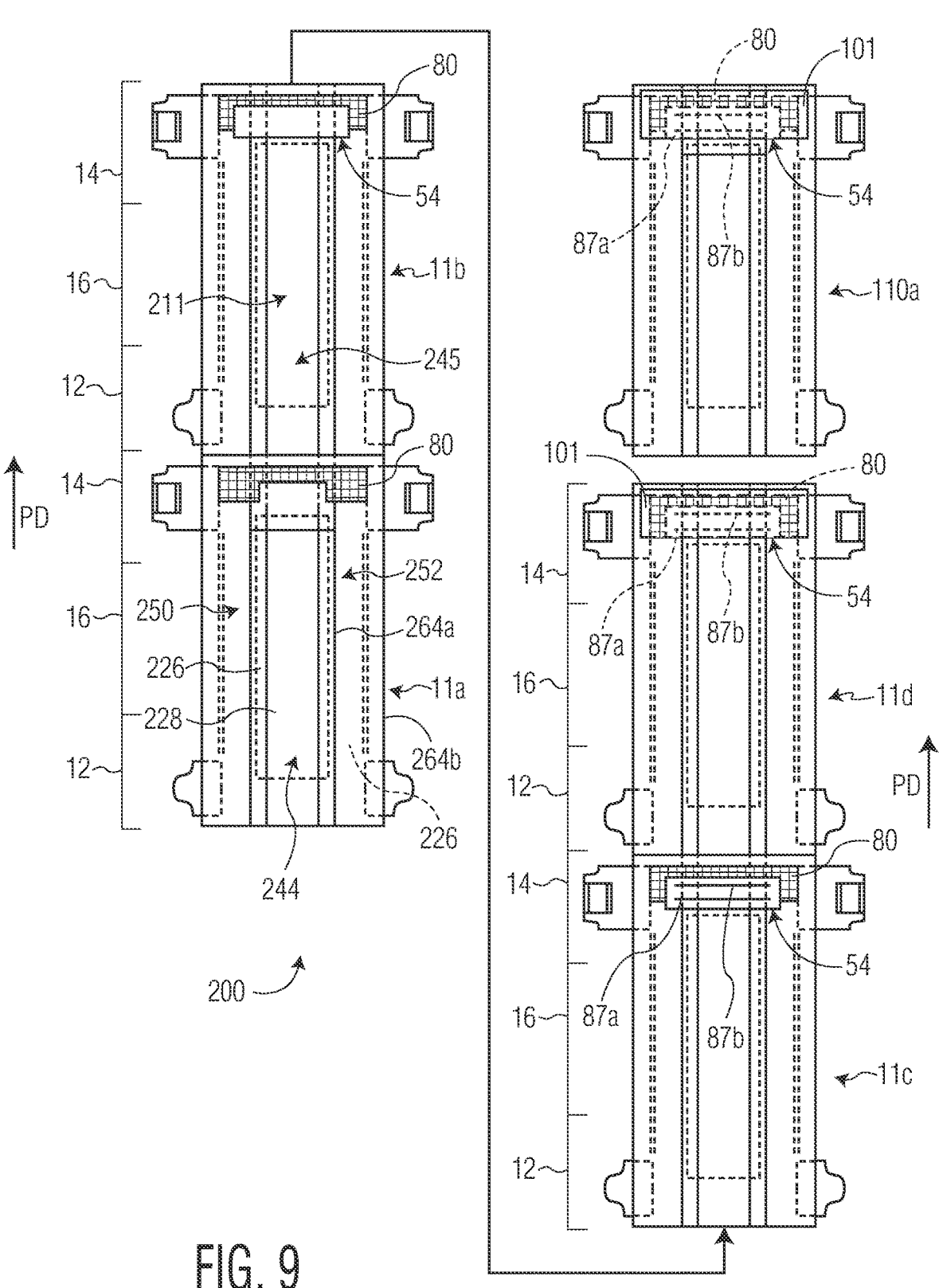

FIG. 9 is a process schematic depicting steps of forming an absorbent article according to aspects of the present disclosure.

Figure 10A:
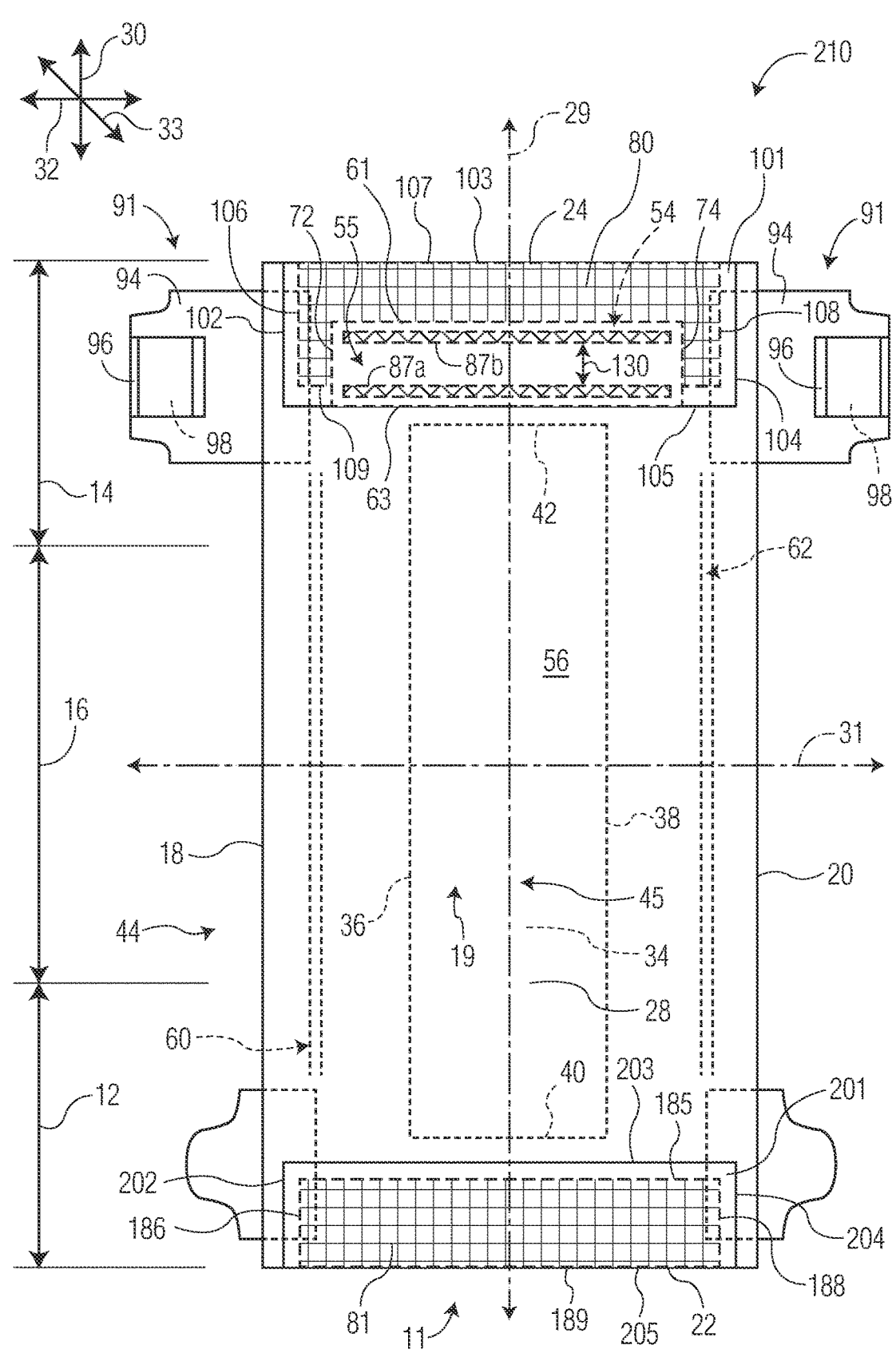

FIG. 10A is a top plan view of an embodiment of an absorbent article in a stretched, laid flat, unfastened condition, according to aspects of the present disclosure.

Figure 10B:
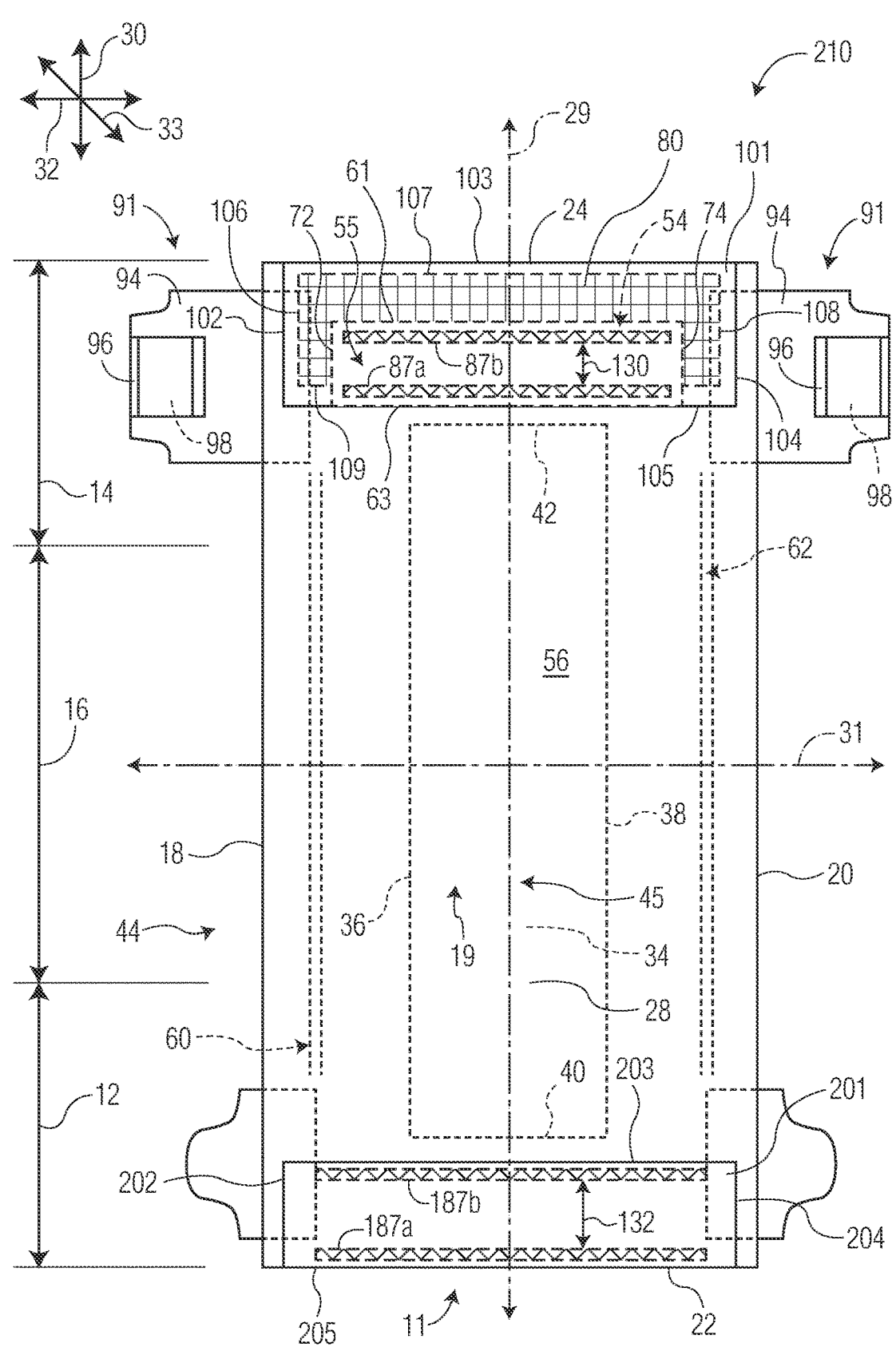

FIG. 10B is a top plan view of another embodiment of an absorbent article in a stretched, laid flat, unfastened condition, according to aspects of the present disclosure.

Figure 11:
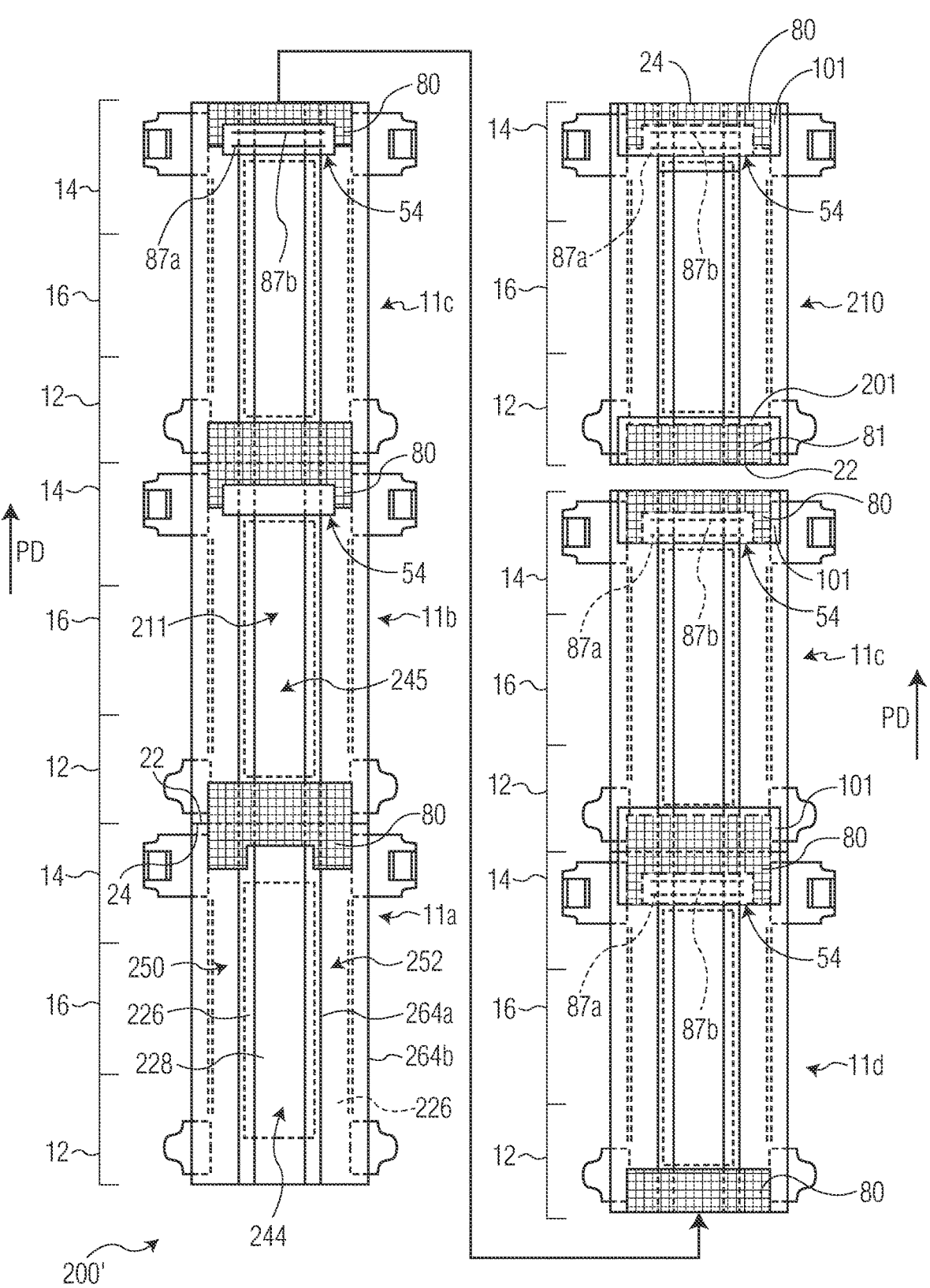

FIG. 11 is a process schematic depicting steps of forming an absorbent article according to aspects of the present disclosure.

Figure 12A:
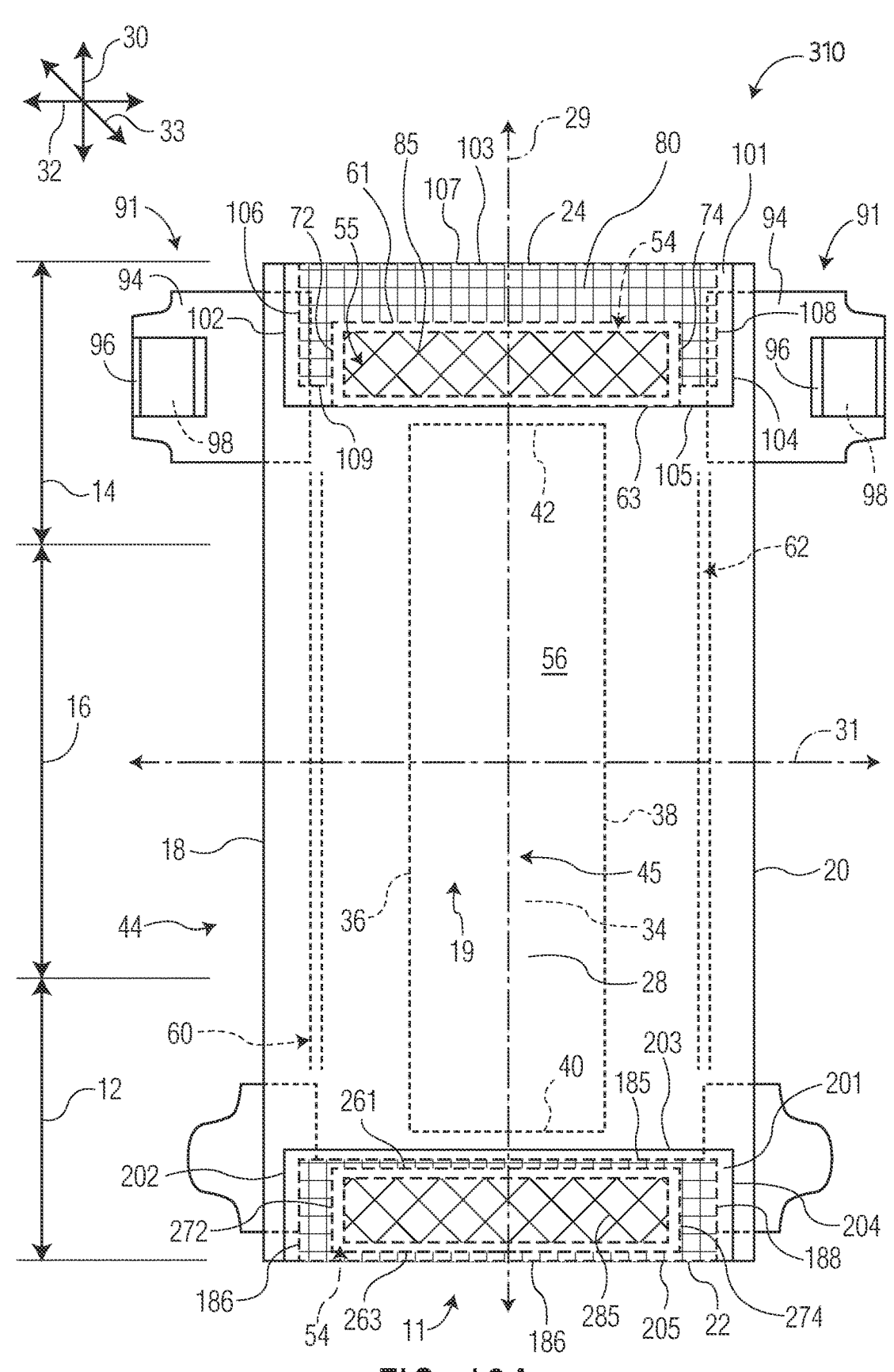

FIG. 12A is a top plan view of an embodiment of an absorbent article in a stretched, laid flat, unfastened condition, according to aspects of the present disclosure.

Figure 12B:
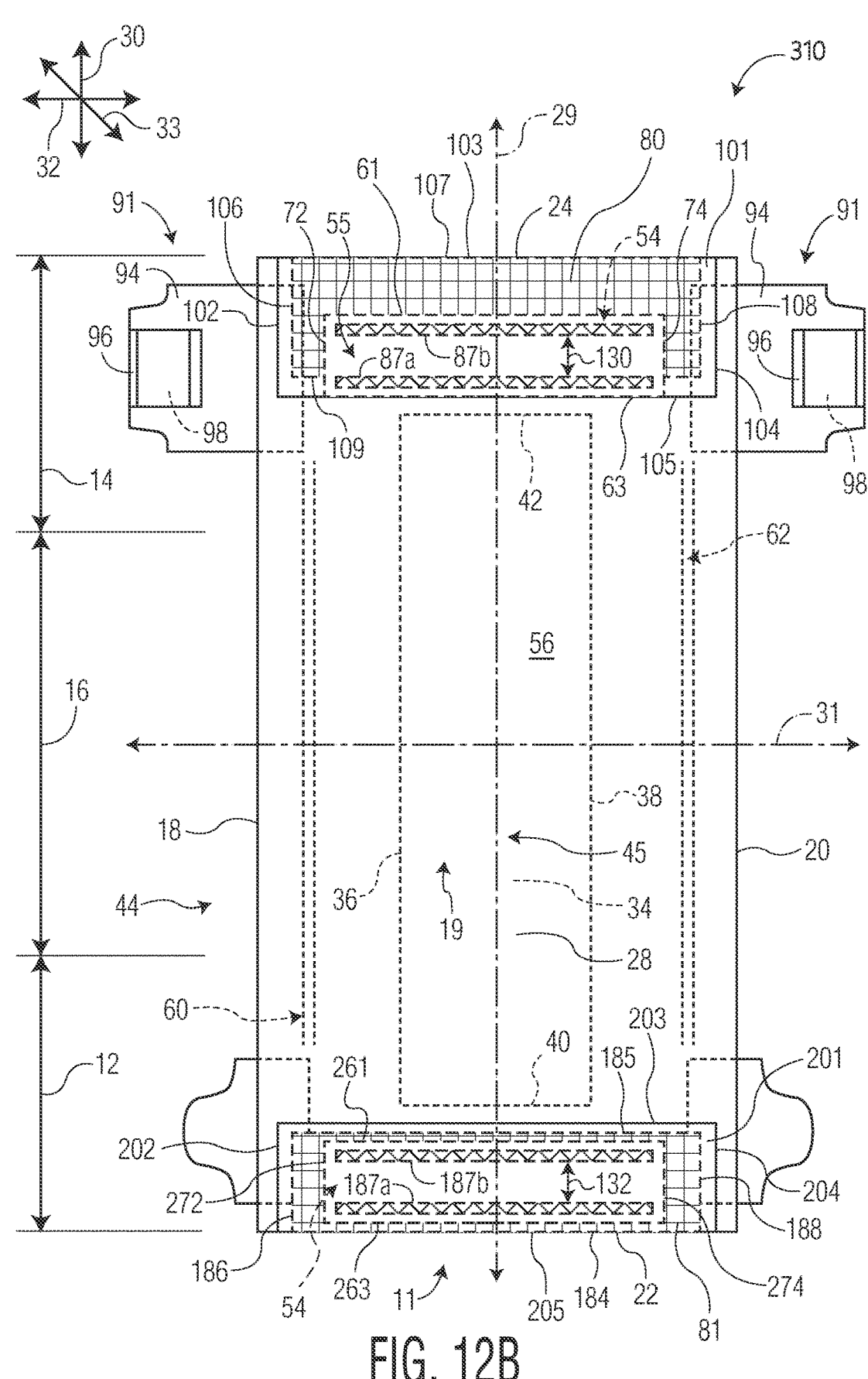

FIG. 12B is a top plan view of another embodiment of an absorbent article in a stretched, laid flat, unfastened condition, according to aspects of the present disclosure.

Figure 13:
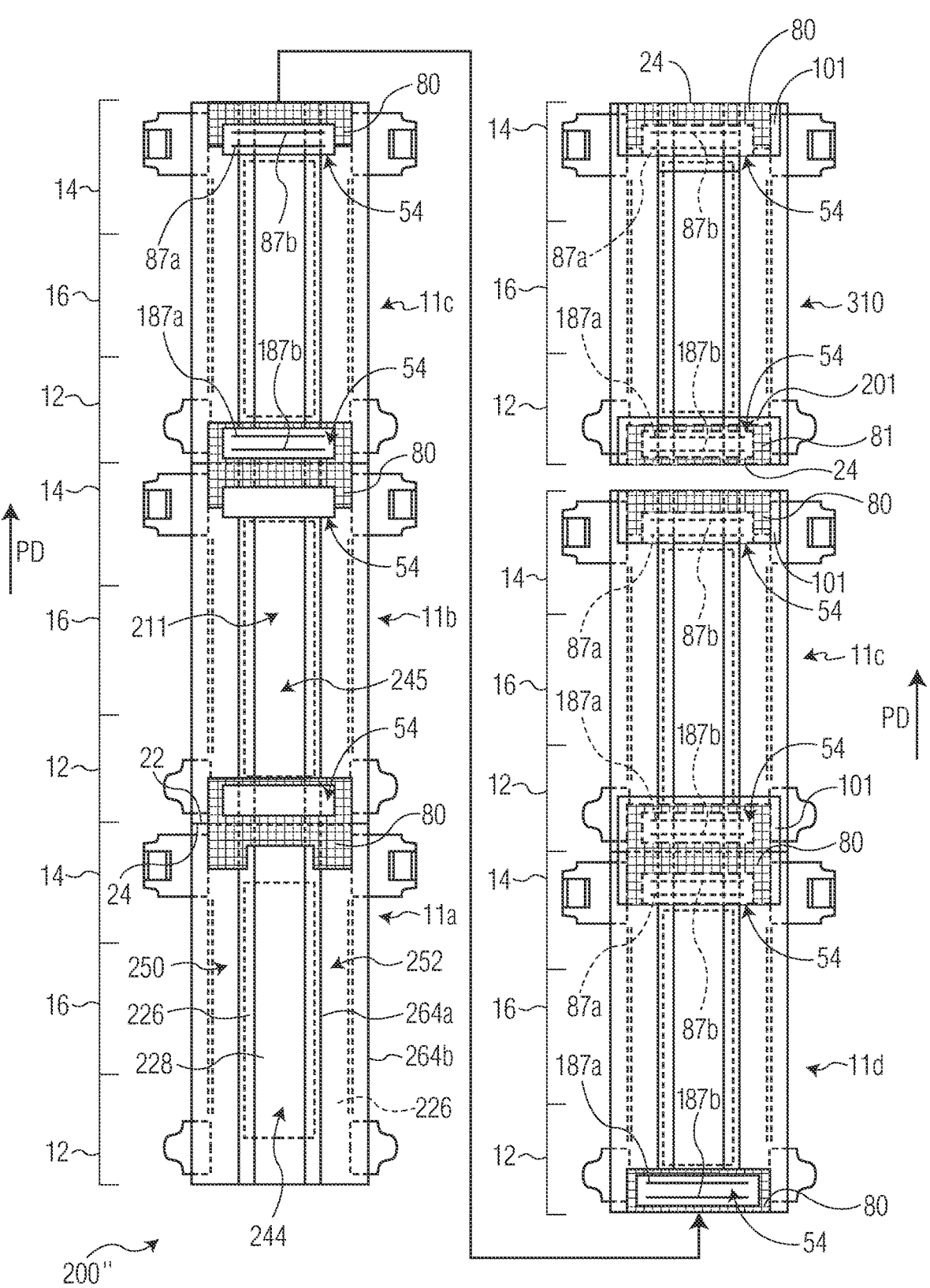

FIG. 13 is a process schematic depicting steps of forming an absorbent article according to aspects of the present disclosure.

Repeat use of reference characters in the present specification and drawings is intended to represent the same or analogous features or elements of the disclosure.

DETAILED DESCRIPTION OF THE DISCLOSURE

In an embodiment, the present disclosure is generally directed towards an absorbent article having an elasticated waist member. Each example is provided by way of explanation and is not meant as a limitation. For example, features illustrated or described as part of one embodiment or figure can be used on another embodiment or figure to yield yet another embodiment. It is intended that the present disclosure include such modifications and variations.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

DEFINITIONS

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads or pants, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" or "coupled" refers herein to the joining, adhering, connecting, attaching, or the like, of two elements. Two elements will be considered bonded or coupled together when they are joined, adhered, connected, attached, or the like, directly to one another or indirectly to one another, such as when each is directly bonded to intermediate elements. The bonding or coupling of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The super-absorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, diaper pant, training pant, youth pant, incontinent product, or other absorbent article about the wearer of one of these absorbent articles. A user and a wearer can be one and the same person.

Absorbent Article:

Referring to FIGS. 1-8, 10, and 12, non-limiting illustrations of exemplary absorbent articles 10, 110a, 110b, 210, and 310 for example, a diaper, are illustrated. Other embodiments of the absorbent article could include training pants, youth pants, adult incontinence garments, and feminine hygiene articles. While the embodiments and illustrations described herein may generally apply to absorbent articles manufactured in the product longitudinal direction, which is hereinafter called the machine direction or process direction manufacturing of a product, it should be noted that one of ordinary skill in the art could apply the information herein to absorbent articles manufactured in the latitudinal direction of the product, which hereinafter is called the cross direction manufacturing of a product, without departing from the spirit and scope of the disclosure.

The absorbent article 10 illustrated in FIGS. 1-4B, the absorbent article 110a, 110b illustrated in FIGS. 5-8, the absorbent article 210 illustrated in FIGS. 10A and 10B, and the absorbent article 310 illustrated in FIGS. 12A and 12B can each include a chassis 11. The absorbent articles 10, 110a, 110b, 210, 310 can include a front waist region 12, a rear waist region 14, and a crotch region 16 disposed between the front waist region 12 and the rear waist region 14 and interconnecting the front and rear waist regions, 12, 14, respectively. The front waist region 12 can be referred to as the front end region, the rear waist region 14 can be referred to as the rear end region, and the crotch region 16 can be referred to as the intermediate region. With respect to an article manufactured in a cross-direction manufacturing process, for example in a three-piece construction, such an absorbent article can have a chassis including a front waist panel defining the front waist region, a rear waist panel defining the rear waist region, and an absorbent panel defining the crotch region. The absorbent panel can extend between the front waist panel and the rear waist panel. In some embodiments, the absorbent panel can overlap the front waist panel and the rear waist panel. The absorbent panel can be bonded to the front waist panel and the rear waist panel to define a three-piece construction. However, it is contemplated that an absorbent article can be manufactured in a cross-direction without being a three-piece construction garment.

The absorbent articles 10, 110a, 110b, 210, 310 can have a pair of longitudinal side edges 18, 20, and a pair of opposite waist edges, respectively designated front waist edge 22 and rear waist edge 24. The front waist region 12 can be contiguous with the front waist edge 22 and the rear waist region 14 can be contiguous with the rear waist edge 24. The longitudinal side edges 18, 20 can extend from the front waist edge 22 to the rear waist edge 24. The longitudinal side edges 18, 20 can extend in a direction parallel to the longitudinal direction 30 for their entire length, such as for the absorbent articles 10, 110a, 110b, 210, 310. In other embodiments, the longitudinal side edges 18, 20 can be curved between the front waist edge 22 and the rear waist edge 24.

The front waist region 12 can include the portion of the absorbent articles 10, 110a, 110b, 210, 310 that, when worn, is positioned at least in part on the front of the wearer while the rear waist region 14 can include the portion of the absorbent articles 10, 110a, 110b, 210, 310 that, when worn, is positioned at least in part on the back of the wearer. The crotch region 16 of the absorbent articles 10, 110a, 110b, 210, 310 can include the portion of the absorbent articles 10, 110a, 110b, 210, 310 that, when worn, is positioned between the legs of the wearer and can partially cover the lower torso of the wearer. The waist edges, 22 and 24, of the absorbent articles 10, 110a, 110b, 210, 310 are configured to encircle the waist of the wearer and together define a central waist opening 23 (as labeled in FIG. 1) for the waist of the wearer. Portions of the longitudinal side edges 18, 20 in the crotch region 16 can generally define leg openings for the legs of the wearer when the absorbent article 10, 110a, 110b, 210, 310 is worn.

The absorbent articles 10, 110a, 110b, 210, 310 can include an outer cover 26 and a bodyside liner 28. The outer cover 26 and the bodyside liner 28 can form a portion of the chassis 11. In an embodiment, the bodyside liner 28 can be bonded to the outer cover 26 in a superposed relation by any suitable means such as, but not limited to, adhesives, ultrasonic bonds, thermal bonds, pressure bonds, or other conventional techniques. As an example, FIGS. 4A and 4B depict the bodyside liner 28 bonded to the outer cover 26 with adhesive 27. The outer cover 26 can define a length in a longitudinal direction 30, and a width in the lateral direction 32, which, in the illustrated embodiment, can coincide with the length and width of the absorbent articles 10, 110a, 110b, 210. As illustrated in FIGS. 2-3B, 5, 6, 10A, 10B, 12A, and 12B, the absorbent articles 10, 110a, 110b, 210, 310 can have a longitudinal axis 29 extending in the longitudinal direction 30 and a lateral axis 31 extending in the lateral direction 32.

The chassis 11 can include an absorbent body 34. The absorbent body 34 can be disposed between the outer cover 26 and the bodyside liner 28. The absorbent body 34 can have longitudinal edges, 36 and 38, which, in an embodiment, can form portions of the longitudinal side edges, 18 and 20, respectively, of the absorbent article 10, 110a, 110b, 210, 310. The absorbent body 34 can have a first end edge 40 that is opposite a second end edge 42, respectively, which, in an embodiment, can form portions of the waist edges, 22 and 24, respectively, of the absorbent articles 10, 110a, 110b, 210. In some embodiments, the first end edge 40 can be in the front waist region 12. In some embodiments, the second end edge 42 can be in the rear waist region 14. In an embodiment, the absorbent body 34 can have a length and width that are the same as or less than the length and width of the absorbent articles 10, 110a, 110b, 210, 310. The bodyside liner 28, the outer cover 26, and the absorbent body 34 can form part of an absorbent assembly 44. In embodiments of articles according to aspects of the present disclosure which are manufactured in a cross-direction manufacturing process, the absorbent panel can form the absorbent assembly 44. The absorbent assembly 44 can also include a fluid transfer layer 46 (for example as shown in FIG. 7) and a fluid acquisition layer (not shown) between the bodyside liner 28 and the fluid transfer layer 46 as is known in the art. The absorbent assembly 44 can also include a spacer layer 48 (for example as shown in FIG. 7) disposed between the absorbent body 34 and the outer cover 26.

The absorbent articles 10, 110a, 110b, 210, 310 can be configured to contain and/or absorb liquid, solid, and semi-solid body exudates discharged from the wearer. In some embodiments, containment flaps 50, 52 can be configured to provide a barrier to the lateral flow of body exudates. To further enhance containment and/or absorption of body exudates, the absorbent articles 10, 110a, 110b, 210, 310 can suitably include an elasticated waist member 54. In some embodiments, the elasticated waist member 54 can be disposed in the rear waist region 14 of the absorbent articles 10, 110a, 110b, 210, 310. Although, it is contemplated that the elasticated waist member 54 can be additionally or alternatively disposed in the front waist region 12 of the absorbent articles 10, 110a, 110b, 210, 310.

The elasticated waist member 54 can be disposed on the body facing surface 19 of the chassis 11 to help contain and/or absorb body exudates. In some embodiments, such as in the absorbent articles 10, 110a, 110b, 210 depicted in FIGS. 2-3B, 5, 6, 10A, 10B, 12A, and 12B, the elasticated waist member 54 can be disposed on the body facing surface 45 of the absorbent assembly 44. In some embodiments, the elasticated waist member 54 can be disposed at least partially on the body facing surface 56 of the bodyside liner 28.

The absorbent articles 10, 110a, 110b, 210, 310 can further include leg elastic members 60, 62 as are known to those skilled in the art. The leg elastic members 60, 62 can be attached to the outer cover 26 and/or the bodyside liner 28 along the opposite longitudinal side edges, 18 and 20, and positioned in the crotch region 16 of the absorbent articles 10, 110a, 110b, 210, 310. The leg elastic members 60, 62 can be parallel to the longitudinal axis 29 as shown in FIGS. 2-3B, 5, 6, 10A, 10B, 12A, and 12B, or can be curved as is known in the art. The leg elastic members 60, 62 can provide elasticized leg cuffs.

Additional details regarding each of these elements of the absorbent articles 10, 110a, 110b, 210, 310 described herein can be found below and with reference to the FIGS. 1-8, 10A, 10B, 12A, and 12B.

Outer Cover:

The outer cover 26 and/or portions thereof can be breathable and/or liquid impermeable. The outer cover 26 and/or portions thereof can be elastic, stretchable, or non-stretchable. The outer cover 26 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the outer cover 26 can be constructed of a microporous polymeric film, such as polyethylene or polypropylene.

In an embodiment, the outer cover 26 can be a single layer of a liquid impermeable material, such as a polymeric film. In an embodiment, the outer cover 26 can be suitably stretchable, and more suitably elastic, in at least the lateral direction 32 of the absorbent article 10, 110a, 110b, 210, 310. In an embodiment, the outer cover 26 can be stretchable, and more suitably elastic, in both the lateral 32 and the longitudinal 30 directions. In an embodiment, the outer cover 26 can be a multi-layered laminate in which at least one of the layers is liquid impermeable. In some embodiments, the outer cover 26 can be a two-layer construction, including an outer layer (not shown) and an inner layer (not shown) which can be bonded together such as by a laminate adhesive. Suitable laminate adhesives can be applied continuously or intermittently as beads, a spray, parallel swirls, or the like, but it is to be understood that the inner layer can be bonded to the outer layer by other bonding methods, including, but not limited to, ultrasonic bonds, thermal bonds, pressure bonds, or the like.

The outer layer of the outer cover 26 can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer of an outer cover 26 can be a 20 gsm spunbond polypropylene non-woven web. The outer layer may also be constructed of the same materials from which the bodyside liner 28 can be constructed as described herein.

The liquid impermeable inner layer of the outer cover 26 (or the liquid impermeable outer cover 26 where the outer cover 26 is of a single-layer construction) can be either vapor permeable (i.e., "breathable") or vapor impermeable. The liquid impermeable inner layer (or the liquid impermeable outer cover 26 where the outer cover 26 is of a single-layer construction) can be manufactured from a thin plastic film. The liquid impermeable inner layer (or the liquid impermeable outer cover 26 where the outer cover 26 is of a single-layer construction) can inhibit liquid body exudates from leaking out of the absorbent articles 10, 110a, 110b, 210, 310 and wetting articles, such as bed sheets and clothing, as well as the wearer and caregiver.

In some embodiments, where the outer cover 26 is of a single layer construction, it can be embossed and/or matte finished to provide a more cloth-like texture or appearance. The outer cover 26 can permit vapors to escape from the absorbent articles 10, 110a, 110b, 210, 310 while preventing liquids from passing through. A suitable liquid impermeable, vapor permeable material can be composed of a microporous polymer film or a non-woven material which has been coated or otherwise treated to impart a desired level of liquid impermeability.

Absorbent Body:

The absorbent body 34 can be suitably constructed to be generally compressible, conformable, pliable, non-irritating to the wearer's skin and capable of absorbing and retaining liquid body exudates. The absorbent body 34 can be manufactured in a wide variety of sizes and shapes (for example, rectangular, trapezoidal, T-shape, I-shape, hourglass shape, etc.) and from a wide variety of materials. The size and the absorbent capacity of the absorbent body 34 should be compatible with the size of the intended wearer (infants to adults) and the liquid loading imparted by the intended use of the absorbent articles 10, 110a, 110b, 210, 310. The absorbent body 34 can have a length and width that can be less than or equal to the length and width of the absorbent articles 10, 110a, 110b, 210, 310.

In an embodiment, the absorbent body 34 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In an embodiment, the absorbent body 34 can be a matrix of cellulosic fluff and superabsorbent material. In further embodiments, the absorbent body 34 can comprise mostly superabsorbent material, or even greater than 80% superabsorbent material, greater than 90% superabsorbent material, or comprise 100% superabsorbent material, by weight of absorbent material of the absorbent body 34. Although, in other embodiments, the absorbent body 34 can be free of superabsorbent material. In an embodiment, the absorbent body 34 may be constructed of a single layer of materials, or in the alternative, may be constructed of two or more layers of materials.

Various types of wettable, hydrophilic fibers can be used in the absorbent body 34. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. Suitable superabsorbent materials can be selected from natural, synthetic, and modified natural polymers and materials. The superabsorbent materials can be inorganic materials, such as silica gels, or organic compounds, such as cross-linked polymers.

If a spacer layer 48 is present, the absorbent body 34 can be disposed on the spacer layer 48 and superposed over the outer cover 26. The spacer layer 48 can be bonded to the outer cover 26, for example, by adhesive. In some embodiments, a spacer layer 48 may not be present and the absorbent body 34 can directly contact the outer cover 26 and can be directly bonded to the outer cover 26. However, it is to be understood that the absorbent body 34 may be in contact with, and not bonded with, the outer cover 26 and remain within the scope of this disclosure. In an embodiment, the outer cover 26 can be composed of a single layer and the absorbent body 34 can be in contact with the singer layer of the outer cover 26. In some embodiments, at least a portion of a layer, such as but not limited to, a fluid transfer layer 46 and/or a spacer layer 48, can be positioned between the absorbent body 34 and the outer cover 26, such as illustrated in FIG. 7. The absorbent body 34 can be bonded to the fluid transfer layer 46 and/or the spacer layer 48.

Bodyside Liner:

The bodyside liner 28 of the absorbent articles 10, 110a, 110b, 210, 310 can overlay the absorbent body 34 and the outer cover 26 and can isolate the wearer's skin from liquid waste retained by the absorbent body 34. In various embodiments, a fluid transfer layer 46 can be positioned between the bodyside liner 28 and the absorbent body 34. In various embodiments, an acquisition layer (not shown) can be positioned between the bodyside liner 28 and the absorbent body 34 or a fluid transfer layer 46, if present. In various embodiments, the bodyside liner 28 can be bonded to the acquisition layer, or to the fluid transfer layer 46 if no acquisition layer is present, via adhesive and/or by a point fusion bonding. The point fusion bonding may be selected from ultrasonic, thermal, pressure bonding, and combinations thereof.

In an embodiment, the bodyside liner 28 can extend beyond the absorbent body 34 and/or a fluid transfer layer 46, if present, and/or an acquisition layer, if present, and/or a spacer layer 48, if present, to overlay a portion of the outer cover 26 and can be bonded thereto by any method deemed suitable, such as, for example, by being bonded thereto by adhesive, to substantially enclose the absorbent body 34 between the outer cover 26 and the bodyside liner 28. It is contemplated that the bodyside liner 28 may be narrower than the outer cover 26. However, in other embodiments, the bodyside liner 28 and the outer cover 26 may be of the same dimensions in width and length, for example, as can be seen in the embodiments illustrated in FIGS. 2-3B, 10A, 10B,

12A, and 12B. In other embodiments, the bodyside liner 28 can be of greater width than the outer cover 26. It is also contemplated that the bodyside liner 28 may not extend beyond the absorbent body 34 and/or may not be secured to the outer cover 26. In some embodiments, the bodyside liner 28 can wrap at least a portion of the absorbent body 34, including wrapping around both longitudinal edges 36, 38 of the absorbent body 34, and/or one or more of the end edges 40, 42. It is further contemplated that the bodyside liner 28 may be composed of more than one segment of material. The bodyside liner 28 can be of different shapes, including rectangular, hourglass, or any other shape. The bodyside liner 28 can be suitably compliant, soft feeling, and non-irritating to the wearer's skin and can be the same as or less hydrophilic than the absorbent body 34 to permit body exudates to readily penetrate through to the absorbent body 34 and provide a relatively dry surface to the wearer.

The bodyside liner 28 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the bodyside liner 28. The bodyside liner 28 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof. The bodyside liner 28 need not be a unitary layer structure, and thus, can include more than one layer of fabrics, films, and/or webs, as well as combinations thereof. For example, the bodyside liner 28 can include a support layer and a projection layer that can be hydroentagled. The projection layer can include hollow projections, such as those disclosed in U.S. Pat. No. 9,474,660 to Kirby, Scott S. C. et al.

For example, the bodyside liner 28 can be composed of a meltblown or spunbond web of polyolefin fibers. Alternatively, the bodyside liner 28 can be a bonded-carded web composed of natural and/or synthetic fibers. The bodyside liner 28 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 28 or it can be selectively applied to particular sections of the bodyside liner 28.

In an embodiment, a bodyside liner 28 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a bodyside liner 28 can be a spunbond substrate with a basis weight from about 10 or 12 to about 15 or 20 gsm. In an embodiment, a bodyside liner 28 can be a 12 gsm spunbond-meltblown-spunbond substrate having 10% meltblown content applied between the two spunbond layers.

Although the outer cover 26 and bodyside liner 28 can include elastomeric materials, it is contemplated that the outer cover 26 and the bodyside liner 28 can be composed of materials which are generally non-elastomeric. In an embodiment, the bodyside liner 28 can be stretchable, and more suitably elastic. In an embodiment, the bodyside liner 28 can be suitably stretchable and more suitably elastic in at least the lateral or circumferential direction of the absorbent articles 10, 110a, 110b, 210, 310. In other aspects, the bodyside liner 28 can be stretchable, and more suitably elastic, in both the lateral and the longitudinal directions 32, 30, respectively.

Containment Flaps:

In an embodiment, the absorbent article 10, 110a, 110b, 210, 310 can include a pair of containment flaps 50, 52. The containment flaps 50, 52 can be formed separately from the absorbent chassis 11 and attached to the chassis 11 or can be formed integral to the chassis 11. In some embodiments, the containment flaps 50, 52 can be secured to the chassis 11 of the absorbent articles 10, 110a, 110b, 210, 310 in a generally parallel, spaced relation with each other laterally inward of the leg openings to provide a barrier against the flow of body exudates. One containment flap 50 can be on a first side of the longitudinal axis 29 and the other containment flap 52 can be on a second side of the longitudinal axis 29. In an embodiment, the containment flaps 50, 52 can extend generally in a longitudinal direction 30 from the front waist region 12 of the absorbent articles 10, 110a, 110b, 210, 310 through the crotch region 16 to the rear waist region 14 of the absorbent article 10. In some embodiments, the containment flaps 50, 52 can extend in a direction substantially parallel to the longitudinal axis 29 of the absorbent articles 10, 110a, 110b, 210, 310, however, in other embodiments, the containment flaps 50, 52 can be curved, as is known in the art.

In embodiments where the containment flaps 50, 52 are coupled to the chassis 11, the containment flaps 50, 52 can be bonded to the bodyside liner 28 with a barrier adhesive 49, as shown in FIG. 7, or the containment flaps 50, 52 can be bonded to the outer cover 26 with a barrier adhesive 49 in some embodiments where the bodyside liner 28 does not extend the full lateral width of the outer cover 26. Of course, the containment flaps 50, 52 can be bonded to other components of the chassis 11 and can be bonded with other suitable means other than a barrier adhesive 49. The containment flaps 50, 52 can be constructed of a fibrous material which can be similar to the material forming the bodyside liner 28. Other conventional materials, such as polymer films, can also be employed.

The containment flaps 50, 52 can each include a base portion 64 and a projection portion 66. The base portion 64 can be bonded to the chassis 11, for example, to the bodyside liner 28 or the outer cover 26 as mentioned above. The base portion 64 can include a proximal end 64a and a distal end 64b. The projection portion 66 can be separated from the base portion 64 at the proximal end 64a of the base portion 64. As used in this context, the projection portion 66 is separated from the base portion 64 at the proximal end 64a of the base portion 64 in that the proximal end 64a of the base portion 64 defines a transition between the projection portion 66 and the base portion 64. The proximal end 64a of the base portion 64 can be located near the barrier adhesive 49. In some embodiments, the distal ends 64*b* of the base portion 64 can laterally extend to the respective longitudinal side edges 18, 20 of the absorbent articles 10, 110*a*, 110*b*, 210, 310. In other embodiments, the distal ends 64*b* of the base portion 64 can end laterally inward of the respective longitudinal side edges 18, 20 of the absorbent articles 10, 110*a*, 110*b*, 210, 310. The containment flaps 50, 52 can also each include a projection portion 66 that is configured to extend away from the body facing surface 19 of the chassis 11 at least in the crotch region 16 when the absorbent articles 10, 110*a*, 110*b*, 210, 310 are in a relaxed configuration, as illustrated in FIG. 7. The containment flaps 50, 52 can include a tack-down region 71 in either or both of the front waist region 12 and the rear waist region 14 where the projection portion 66 is coupled to the body facing surface 19 of the chassis 11.

It is contemplated that the containment flaps 50, 52 can be of various configurations and shapes, and can be constructed by various methods. For example, the containment flaps 50, 52 of FIGS. 2-3B, 10A, 10B, 12A, and 12B depict a longitudinally extending containment flap 50, 52 with a tack-down region 71 in both the front and rear waist regions 12, 14 where the projection portion 66 of each containment flap 50, 52 is tacked down to the bodyside liner 28 towards or away from the longitudinal axis 29 of the absorbent articles 10, 110*a*, 110*b*, 210, 310. However, the containment flaps 50, 52 can include a tack-down region 71 where the projection portion 66 of each of the containment flaps 50, 52 is folded back upon itself and coupled to itself and the bodyside liner 28 in a "C-shape" configuration, as is known in the art and described in U.S. Pat. No. 5,895,382 to Robert L. Popp et al. As yet another alternative, it is contemplated that the containment flaps 50, 52 could be constructed in a "T-shape" configuration, such as described in U.S. Pat. No. 9,259,362 to Robert L. Popp et al. Such a configuration can also include a tack-down region 71 in either or both of the front and rear waist regions 12, 14, respectively. Of course, other configurations of containment flaps 50, 52 can be used in the absorbent articles 10, 110*a*, 110*b*, 210, 310 and still remain within the scope of this disclosure.

The containment flaps 50, 52 can include one or more flap elastic members 68, such as the two flap elastic strands depicted in FIGS. 2-3B, 5-7, 10A, 10B, 12A, and 12B. Suitable elastic materials for the flap elastic members 68 can include sheets, strands or ribbons of natural rubber, synthetic rubber, or thermoplastic elastomeric materials. Of course, while two elastic members 68 are shown in each containment flap 50, 52, it is contemplated that the containment flaps 50, 52 can be configured with one or three or more elastic members 68. Alternatively or additionally, the containment flaps 50, 52 can be composed of a material exhibiting elastic properties itself.

The flap elastic members 68, as illustrated in FIGS. 2-3B, 6, 10A, 10B, 12A, and 12B, can have two strands of elastomeric material extending longitudinally in the projection portion 66 of the containment flaps 50, 52, in generally parallel, spaced relation with each other. The elastic members 68 can be within the containment flaps 50, 52 while in an elastically contractible condition such that contraction of the strands gathers and shortens the projection portions 66 of the containment flaps 50, 52 in the longitudinal direction 30. As a result, the elastic members 68 can bias the projection portions 66 of the containment flaps 50, 52 to extend away from the body facing surface 45 of the absorbent assembly 44 in a generally upright orientation of the containment flaps 50, 52, especially in the crotch region 16 of the absorbent articles 10, 110*a*, 110*b*, 210, 310, when the absorbent article 10 is in a relaxed configuration.

During manufacture of the containment flaps 50, 52 at least a portion of the elastic members 68 can be bonded to the containment flaps 50, 52 while the elastic members 68 are elongated. The percent elongation of the elastic members 68 can be, for example, about 110% to about 350%. The elastic members 68 can be coated with adhesive while elongated to a specified length prior to attaching to the elastic members 68 to the containment flaps 50, 52. In a stretched condition, the length of the elastic members 68 which have adhesive coupled thereto can provide an active flap elastic region 70 in the containment flaps 50, 52, as labeled in FIG. 2, which will gather upon relaxation of the absorbent article 10. The active flap elastic region 70 of containment flaps 50, 52 can be of a longitudinal length that is less than the length of the absorbent articles 10, 110*a*, 110*b*, 210, 310. In this exemplary method of bonding the elastic members 68 to the containment flaps 50, 52, the portion of the elastic members 68 not coated with adhesive will retract after the elastic members 68 and the absorbent article 10 are cut in manufacturing to form an individual absorbent article 10, 110*a*, 110*b*, 210, 310. As noted above, the relaxing of the elastic members 68 in the active flap elastic region 70 when the absorbent article 10, 110*a*, 110*b*, 210, 310 is in a relaxed condition can cause each containment flap 50, 52 to gather and cause the projection portion 66 of each containment flap 50, 52 to extend away from the body facing surface 19 of the chassis 11 (e.g., the body facing surface 45 of the absorbent assembly 44 or the body facing surface 56 of the bodyside liner 28), as depicted in FIG. 7.

Of course, the elastic members 68 can be bonded to the containment flaps 50, 52 in various other ways as known by those of skill in the art to provide an active flap elastic region 70, which is within the scope of this disclosure. Additionally, the active flap elastic regions 70 can be shorter or longer than depicted herein, including extending to the front waist edge 22 and the rear waist edge 24, and still be within the scope of this disclosure.

Leg Elastics:

Leg elastic members 60, 62 can be secured to the outer cover 26, such as by being bonded thereto by laminate adhesive, generally laterally inward of the longitudinal side edges, 18 and 20, of the absorbent article 10, 110*a*, 110*b*, 210, 310. The leg elastic members 60, 62 can form elasticized leg cuffs that further help to contain body exudates. In an embodiment, the leg elastic members 60, 62 may be disposed between inner and outer layers (not shown) of the outer cover 26 or between other layers of the absorbent article 10, for example, between the base portion 64 of each containment flap 50, 52 and the bodyside liner 28 as depicted in FIG. 7, between the base portion 64 of each containment flap 50, 52 and the outer cover 26, or between the bodyside liner 28 and the outer cover 26. The leg elastic members 60, 62 can be one or more elastic components near each longitudinal side edge 18, 20. For example, the leg elastic members 60, 62 as illustrated herein each include two elastic strands. A wide variety of elastic materials may be used for the leg elastic members 60, 62. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate. Additionally, it is contemplated that the leg elastic members 60, 62 can be formed with the containment flaps 50, 52, and then attached to the chassis 11 in some embodiments. Of course, the leg elastic members 60, 62 can be omitted from the absorbent article 10, 110*a*, 110*b*, 210, 310 without departing from the scope of this disclosure.

Elasticated Waist Member:

In an embodiment, the absorbent articles 10, 110*a*, 110*b*, 210, 310 can have one or more elasticated waist members 54. The elasticated waist member(s) 54 can be disposed in the rear waist region 14 as illustrated in FIGS. 1-11B, or in both the rear waist region 14 and the front waist region 12, as illustrated in FIGS. 12A, 12B. Although generally described in the present disclosure with reference to a singular elasticated waist member, it should be understood that such description applies equally to each elasticated waist member in embodiments which contain multiple elasticated waist members 54. As will be discussed in more detail below, the elasticated waist member 54 can help contain and/or absorb body exudates, especially low viscosity fecal matter, and as such, can be preferred to be in the rear waist region 14. An elasticated waist member 54 in the front waist region 12 can help contain and/or absorb body exudates, such as urine, in the front waist region 12. Although not as prevalent as in the rear waist region 14, in some circumstances, fecal material may also spread to the front waist region 12, and thus, an elasticated waist member 54 disposed in the front waist region 12 can help contain and/or absorb body exudates as well. According to aspects of the present disclosure, various of the embodiments of articles 10, 110*a*, 110*b*, 210, and 310 may further include a waist region covering material 101, 201 in the rear waist region 14 (and optionally the front waist region 12) which may be coupled to the elasticated waist member 54 to provide for increased comfort.

The elasticated waist member 54 can include a first longitudinal side edge 72 and a second longitudinal side edge 74, as shown in FIG. 2. The elasticated waist member 54 can further comprise a lateral top edge 61 disposed proximate the rear waist edge 24 and a lateral bottom edge 63 disposed closer to the crotch region 16 than the lateral top edge 61, along with a body facing surface 55. The first longitudinal side edge 72 can be opposite from the second longitudinal side edge 74. The distance between the first longitudinal side edge 72 and the second longitudinal side edge 74 can define a width of the elasticated waist member 54 in the lateral direction 32. Although not depicted, in some embodiments, the first longitudinal side edge 72 can substantially align with the first longitudinal side edge 18 of the absorbent articles 10, 110*a*, 110*b*, 210, 310. Similarly, in some embodiments, the second longitudinal side edge 74 can align with the second longitudinal side edge 20 of the absorbent articles 10, 110*a*, 110*b*, 210, 310. In further embodiments, the first longitudinal side edge 72 and the second longitudinal side edge 74 may not align with the first longitudinal side edge 18 of the absorbent articles 10, 110*a*, 110*b*, 210, 310, but may overlap a portion of the back fastener(s) 91 which are coupled to the chassis 11. As illustrated most clearly in FIG. 2, the elasticated waist member 54 can be configured such that the first longitudinal side edge 72 can be disposed laterally outward of the proximal end 64*a* of the base portion 64 of the containment flap 50. Similarly, the elasticated waist member 54 can be configured such that the second longitudinal side edge 74 can be disposed laterally outward of the proximal end 64*a* of the base portion 64 of the containment flap 52.

The elasticated waist member 54 can be comprised of a variety of materials. In a preferred embodiment, the elasticated waist member 54 can be comprised of a spunbond-meltblown-spunbond ("SMS") material. However it is contemplated that the elasticated waist member 54 can be comprised of other materials including, but not limited to, a spunbond-film-spunbond ("SFS"), a bonded carded web ("BCW"), or any non-woven material. In some embodiments, the elasticated waist member 54 can be comprised of a laminate of more than one of these exemplary materials, or other materials. In some embodiments, the elasticated waist member 54 can be comprised of a liquid impermeable material, for example a film material. In some embodiments, the elasticated waist member 54 can be comprised of a material coated with a hydrophobic coating. The basis weight of the material forming the elasticated waist member 54 can vary, however, in a preferred embodiment, the basis weight can be between about 8 gsm to about 120 gsm, not including the elastic members 86 in the elasticated waist member 54. More preferably, the basis weight of the material comprising the elasticated waist member 54 can be between about 10 gsm to about 40 gsm, and even more preferably, between about 15 gsm to about 25 gsm.

In preferred embodiments, the elasticated waist member 54 can include at least one elastic member 86. In some embodiments, such as the embodiments depicted in FIGS. 2, 4A, and 4B, the elasticated waist member 54 can include multiple elastic members 86, such as five elastic members 86. Of course, it is contemplated that the elasticated waist member 54 can include other amounts of elastic members 86, such as three, four, six, eight, or ten elastic members, and in some embodiments, no elastic members 86. The elastic member 86 can span substantially from the first longitudinal side edge 72 to the second longitudinal side edge 74 of the elasticated waist member 54. In some embodiments, the elastic members 86 can be spaced evenly in the longitudinal direction 30. At least one of the elastic members 86 can be disposed located near a lateral bottom edge 63 of the elasticated waist member 54.

A wide variety of elastic materials may be used for the elastic member(s) 86 in the elasticated waist member 54. Suitable elastic materials can include sheets, strands or ribbons of natural rubber, synthetic rubber, thermoplastic elastomeric materials, or elastic foams. The elastic materials can be stretched and secured to a substrate forming the elasticated waist member 54, secured to a gathered substrate, or secured to a substrate and then elasticized or shrunk, for example, with the application of heat, such that the elastic retractive forces are imparted to the substrate forming the elasticated waist member 54.

In some embodiments, the elasticated waist member 54 can be disposed on the body facing surface 45 of the absorbent assembly 44. In some embodiments, such as in embodiments illustrated in FIGS. 1-8, 10A, 10B, 12A, and 12B, the elasticated waist member 54 can be disposed on the body facing surface 56 of the bodyside liner 28. The elasticated waist member 54 can be coupled to the chassis 11 by being placed either over the containment flaps 50, 52 or under the containment flaps 50, 52. More specifically, the elasticated waist member 54 can be disposed on the body facing surface 19 of the chassis 11 such that the elasticated waist member 54 is disposed over the base portion 64 of the first and the second containment flaps 50, 52, respectively. Alternatively, the elasticated waist member 54 can be disposed on the body facing surface 19 of the chassis 11 such that the elasticated waist member 54 is disposed under the base portion 64 of the first and the second containment flaps 50, 52, respectively. Both configurations can provide advantages to the functioning of the elasticated waist member 54 to contain and/or absorb body exudates.

Fastening System:

In an embodiment, the absorbent articles 10, 110, 210, 310 can include a fastening system. The fastening system can include one or more back fasteners 91 and one or more front fasteners 92. The embodiments being shown in FIGS. 1, 2, 9A, 9B, 11A, and 11B depict embodiments with one front fastener 92. Portions of the fastening system may be included in the front waist region 12, rear waist region 14, or both.

The fastening system can be configured to secure the absorbent articles 10, 110, 210, 310 about the waist of the wearer in a fastened condition as shown in FIG. 1 and help maintain the absorbent articles 10, 110, 210, 310 in place during use. In an embodiment, the back fasteners 91 can include one or more materials bonded together to form a composite ear as is known in the art. For example, the composite fastener may be composed of a stretch component 94, a nonwoven carrier or hook base 96, and a fastening component 98, as labeled in FIGS. 2-3B, 9A, 9B, 11A, and 11B. In some embodiments the elasticated waist member 54 can laterally extend to the back fasteners 91, and/or to each of the longitudinal side edges 18, 20 of the absorbent articles 10, 110, 210, 310. In some embodiments, the elasticated waist member 54 can be coupled to the stretch component 94 of the back fasteners 91, either directly or indirectly.

Waist Region Covering Material:

According to some embodiments of the present disclosure, the absorbent articles 10, 110a, 110b, 210, 310 can include a waist region covering material 101 disposed in the rear region 14. The waist region covering material 101 may be coupled to the body facing surface 19 of the chassis 11, and more specifically in some embodiments, the body facing surface 56 of the bodyside liner 28. The waist region covering material 101 may further be coupled to the elasticated waist member 54. The specific attachment of the waist region covering material 101 is described in more detail below.

Where the waist region covering material 101 is disposed at least partially over the elasticated waist member 54, the waist region covering material 101 may help to mitigate forces applied to a wearer by the elastic members 86 of the elasticated waist member 54. For example, because the elastic members 86 are under tension when the absorbent articles 10, 110a, 110b, 210, 310 are worn, to help provide close contact with the wearer's skin, the elastomeric strands 86 and provide pressure to a wearer's skin. By virtue of the waist region covering material 101 being disposed between the elasticated waist member 54 and a wearer's skin, the waist region covering material 101 provides a dampening effect on such forces, while still providing for close contact of the article, e.g. article 10, 110a, 110b, 210, 310, with a wearer's skin.

Typically, such a waist region covering material 101 may comprise a soft and/or cushiony material, thereby additionally helping to provide an improved feeling of comfort to a wearer. Example suitable materials for waist region covering material 101 include TABCW materials having basis weight ranges between 10 gsm and 50 gsm. According to some preferred embodiments, such TABCW materials may have basis weights between 15 gsm and gsm. Although, it should be understood that other materials can be suitable for use as waist region covering material 101. Some further examples include spunbond materials—including SMS materials, hydroentangled materials, bonded carded webs, and the like.

According to some embodiments, material loft may be important to achieving a desired softness of the waist region covering material 101. In some embodiments, a loft of the waist region covering material 101 may be greater than 0.5 mm. Although, in other preferred embodiments, a loft of the waist region covering material 101 may be greater than 1.0 mm, greater than 1.5 mm, greater than 2.0 mm, or greater than 2.5 mm.

The waist region covering material 101 has a first longitudinal side edge 102 and a second longitudinal side edge 104 along with a top lateral edge 103 and a bottom lateral edge 105. The top lateral edge 103 is disposed proximate the rear waist edge 24 while the bottom lateral edge 105 is disposed closer to the crotch region 16 than the top lateral edge 103. According to at least the embodiments of FIGS. 2-3B, the waist region covering material 101 may fully cover the elasticated waist member 54. For example, the top lateral edge 103 may be disposed closer to the rear waist edge 24 than the lateral top edge 61 of the elasticated waist member 54. Additionally, the first longitudinal side edge 102 and the second longitudinal side edge 104 of the waist region covering material 101 may be disposed outboard of the first longitudinal side edge 72 and the second longitudinal side edge 74, respectively. In some of these embodiments, the bottom lateral edge 105 of the waist region covering material 101 is disposed closer to the crotch region 16 than the lateral bottom edge 63 of the elasticated waist member 54. In other embodiments, the bottom lateral edge 105 may be disposed at approximately the same position as the lateral bottom edge 63 such that the bottom lateral edge 105 and the lateral bottom edge 63 overlap in the vertical direction 33. In still further embodiments, the top lateral edge 103 may be disposed at approximately the same position as the lateral top edge 61 such that the top lateral edge 103 and the lateral top edge 61 overlap in the vertical direction 33. Similarly, one or both of the first longitudinal side edge 102 and the second longitudinal side edge 104 of the waist region covering material 101 may be approximately aligned with the first longitudinal side edge 72 and/or the second longitudinal side edge 74. In this manner, the waist region covering material 101 may provide additional comfort to a wearer. The waist region covering material 101 further may allow the elasticated waist member 54 to be formed of materials consider harsh or uncomfortable against skin, but which have superior liquid impermeability properties—for example film materials.

Although, in further embodiments, the waist region covering material 101 may not cover the elasticated waist member 54 completely, as much of the comfort benefit of the waist region covering material 101 can be achieved by only partially covering the elasticated waist member 54. For example, the lateral bottom edge 63 of the elasticated waist member 54 may be disposed closer to the crotch region 16 than the bottom lateral edge 105 of the waist region covering material 101 in some embodiments. Alternatively or additionally, the lateral top edge 61 may be disposed closer to the rear waist edge 24 than the top lateral edge 103. Likewise, one or both of the first longitudinal side edge 102 and the second longitudinal side edge 104 of the waist region covering material 101 may be disposed inboard of the first longitudinal side edge 72 and/or the second longitudinal side edge 74.

According to at least the embodiments of FIGS. 2-4B, the top lateral edge 103 of the waist region covering material 101 may extend toward the rear waist edge 24 of the article 10, but may be spaced a small distance from the rear waist edge 24. FIGS. 3A and 3B depict a close-up portion of different embodiments of the exemplary article 10 along with a number of features removed to more clearly highlight the elasticated waist member 54, the waist region covering material 101, and how these features are coupled together and to the chassis 11. FIGS. 4A and 4B depict cross-section views of the exemplary article 10, as viewed along line 4-4. In such embodiments, the waist region covering material 101 may be cut and placed onto the chassis 11. In such types of cut and place manufacturing processes, it can be difficult to align material edges exactly. Accordingly, the top lateral edge 103 of the waist region covering material 101 may be spaced anywhere between 2.5 mm and 15 mm, or between 4 mm and 10 m, or between 5 mm and 8 mm, from the rear waist edge 24. Likewise, the first longitudinal side edge 102 and a second longitudinal side edge 104 may be spaced from the respective longitudinal side edges 18, 20 of the chassis 11 as opposed to extending all the way to the longitudinal side edges 18, 20.

Figure 3A:
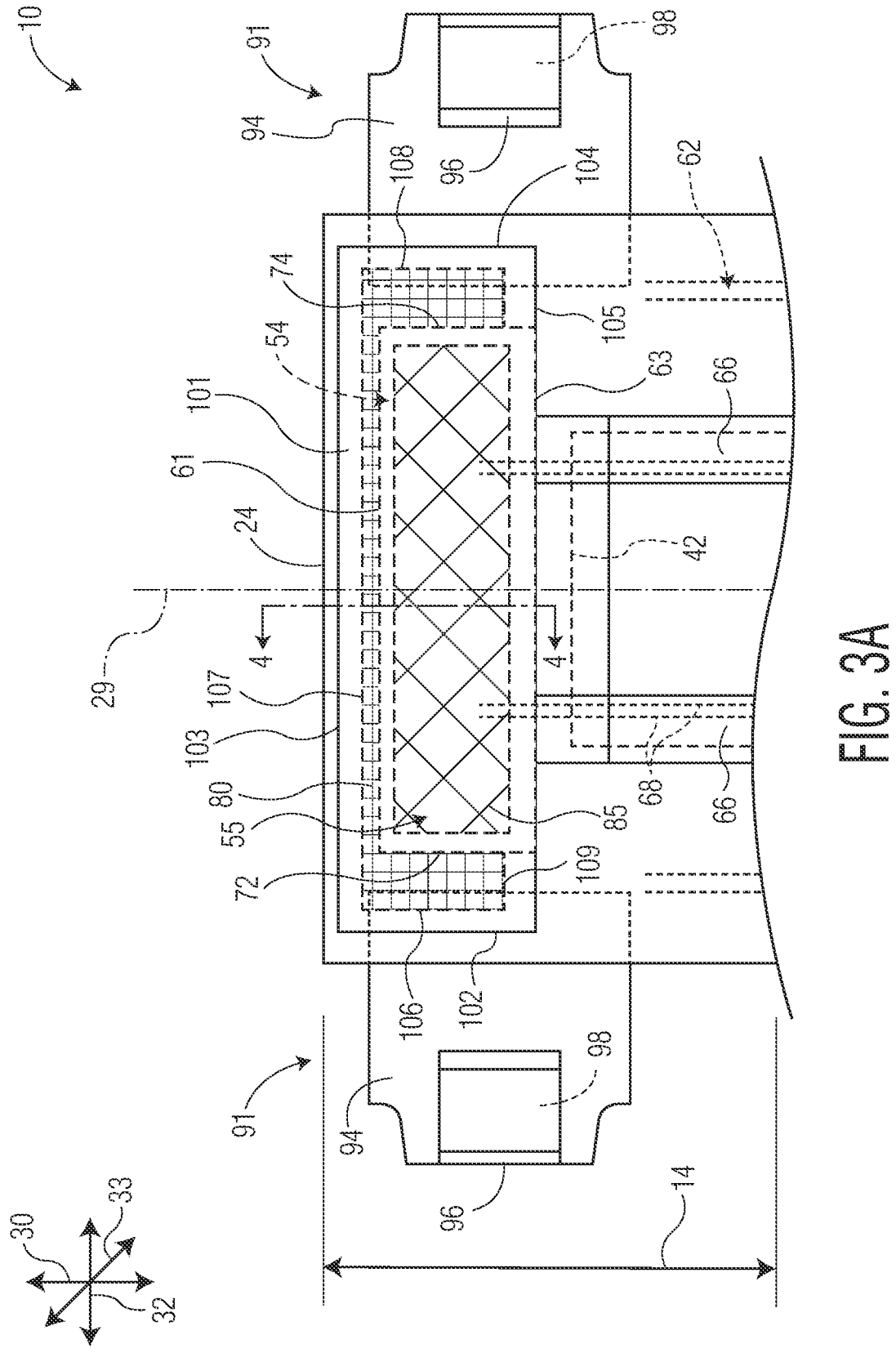
FIG. 3A is a close-up of an embodiment of the rear waist region of the article of FIG. 1, with components removed to more clearly illustrate features according to aspects of the present disclosure.

As can be seen most clearly in FIGS. 3A-4B, both the elasticated waist member 54 and the waist region covering material 101 may be coupled to the body facing surface 19 of the chassis 11 by adhesive 80. Adhesive 80 is disposed over a region of the body facing surface 19 with the region having a top lateral edge 107, a bottom lateral edge 109, and side longitudinal edges 106, 108. As illustrated in FIG. 3A with a portion of the region 80 hidden by the elasticated waist member 54, the edges 107, 109, 106, and 108 are generally spaced from the edges 102, 104, 103, and 105 of the waist region covering material 101 such that the waist region covering material 101 fully covers the region of adhesive 80. Although, in some embodiments, the bottom lateral edge 109 may be left uncovered by the waist region covering material 101, but be covered by the elasticated waist member 54, or left uncovered by the elasticated waist member 54, but be covered by the waist region covering material 101. It may be undesirable to leave the region of adhesive 80 uncovered by both of the waist region covering material 101 and the elasticated waist member 54, or another material layer, as the uncovered adhesive 80 may cause the article 10 to stick together in a folded state and/or cause tearing of one or more of the layers of the article 10 when the article 10 is unfolded.

The waist region covering material 101 may also be coupled to the elasticated waist member 54, for example by adhesive 85, as depicted in FIGS. 3A and 4A. In embodiments according to FIGS. 3A and 4A, the adhesive 85 may comprise a continuous region disposed on top of the elasticated waist member 54. Although not labeled specifically, the region bounded by the adhesive 85 may likewise have top, bottom, and longitudinal side edges. Such side edges may be generally spaced inward from corresponding top, bottom, and longitudinal side edges 61, 63, 72, and 74 of the elasticated waist member 54. Although, this may not necessarily be the case in all embodiments. For example, at least with respect to edges 61, 72, and 74, if the region bounded by adhesive 85 extends beyond the edges 61, 72, or 74, the adhesive 85 would overlay and contact the adhesive 80, and would ultimately be covered by the waist region covering material 101. In embodiments where the bottom lateral edge 105 of the waist region covering material 101 does not extend closer to the crotch region 16 than the lateral bottom edge 63 of the elasticated waist member 54, it may be important for a bottom edge of the region bounded by adhesive 85 to not extend closer to the crotch region 16 than the lateral bottom edge 63 of the elasticated waist member 54.

Figure 3B:
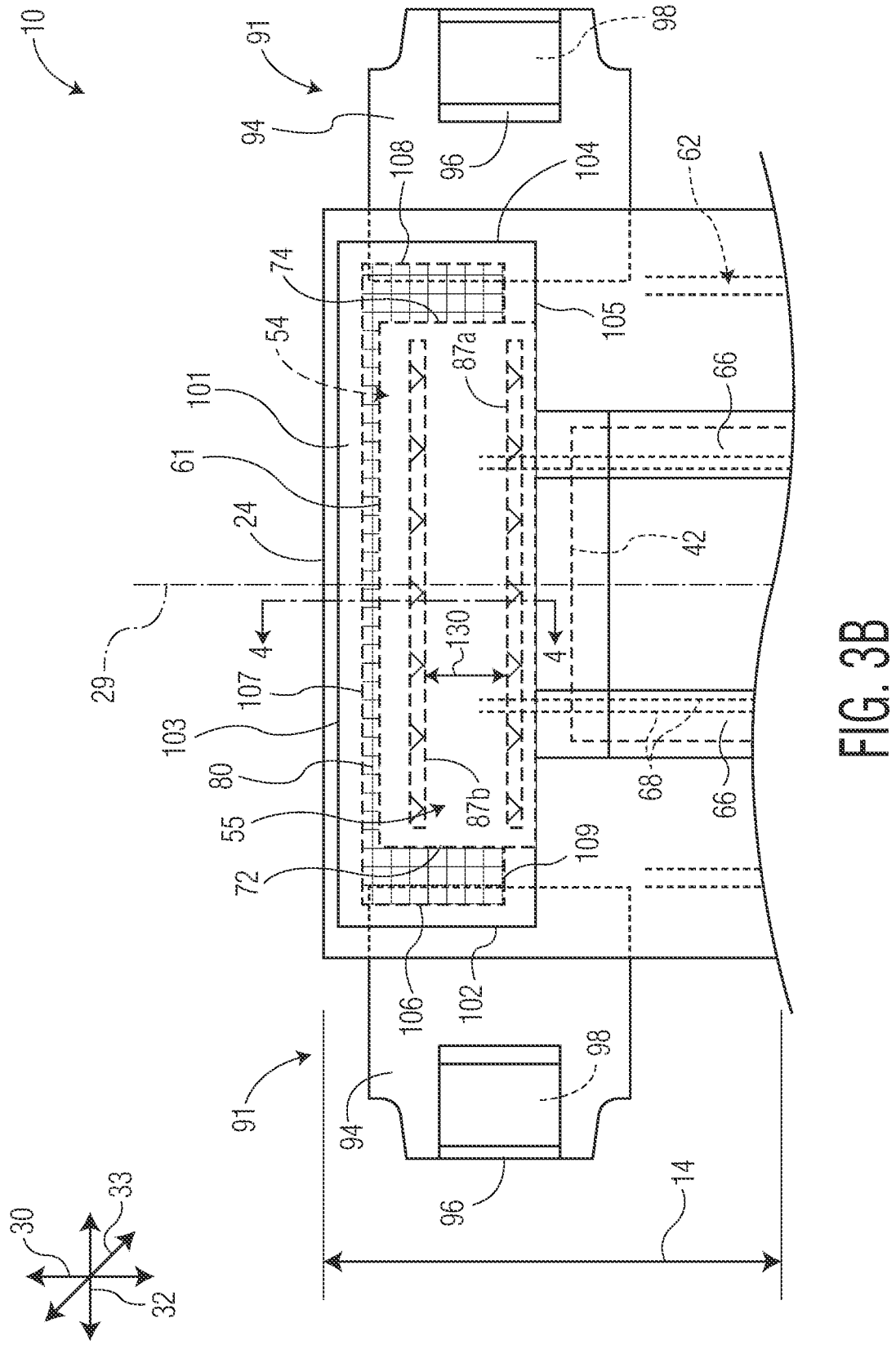
FIG. 3B is a close-up of an additional embodiment of the rear waist region of the article of FIG. 1, with components removed to more clearly illustrate features according to aspects of the present disclosure.

In alternative embodiments, the material 101 may be coupled to the elasticated waist member 54 by at least a first connection and a second connection, for example by adhesives 87a, 87b, as depicted in FIGS. 3B and 4B. According to embodiments related to FIGS. 3B and 4B, the adhesives 87a, 87b may be lines or stripes of adhesives with adhesive 87a disposed proximate the lateral bottom edge 63 of the elasticated waist member 54 and the adhesive 87b disposed proximate the lateral top edge 61. The adhesives 87a, 87b may have longitudinal lengths 121, 123 extending in the longitudinal direction 30. Of course, the longitudinal lengths 121, 123 need not be the same, but both lengths 121, 122 may generally fall between 2 mm and 10 mm in length, or between 2 mm and 5 mm in length in other embodiments. Additionally, the adhesives 87a, 87b may be spaced distances 125, 127 from the lateral bottom edge 63 and lateral top edge 61 of the elasticated waist member 54, respectively. Similarly, the distances 125, 127 need not be the same, but both may generally fall between 2 mm and 10 mm, or between 2 mm and 5 mm in other embodiments. Generally, the distances 125, 127 may be chosen so as to allow for variations in the process of constructing article 10 while still ensuring that the adhesives 87a, 87b are disposed on the elasticated waist member 54. Further embodiments are contemplated which include connections in addition to adhesives 87a, 87b—for example, one, two, three, four, or more additional connections, such as additional lines or regions of adhesive.

Additionally, a combination of lengths 121, 122 and distances 125, 127 may be chosen to provide an unbonded region 130 between the adhesives 87a, 87b (and any other connections between the waist region covering material 101 and the elasticated waist member 54) where the waist region covering material 101 is uncoupled from the elasticated waist member 54. Such an unbonded region 130 may provide a benefit of allowing the waist region covering material 101 to flex away from the elasticated waist member 54 which can decrease any potential fluid transfer between the waist region covering material 101 and the elasticated waist member 54, thereby helping to ensure dry, comfortable skin for a user even where fluid may soak into the elasticated waist member 54. Additionally, the unbonded region 130 may provide for an increased feeling of softness by a wearer, particularly where the waist region covering material 101 is softer and/or more flexible than the elasticated waist member 54. According to aspects of the present disclosure, the longitudinal length of the unbonded region 130 may generally be desired to be greater than 10 mm. In other embodiments, the unbonded region 130 may be greater than 15 mm, or greater than 20 mm, or greater than 25 mm, or greater than 30 mm, or greater than 35 mm, or greater than 40 mm, or greater than 50 mm. The unbonded region 130 may generally be less than 75 mm or less than 65 mm in any of the above embodiments.

FIGS. 5-8 depict exemplary absorbent articles 110a, 110b according to the present disclosure. In such embodiments according to FIGS. 5-8, the elasticated waist member 54 may be additionally configured to form a pocket for helping to contain body exudate. FIGS. 5 and 6 depict close-ups of the rear region of the articles 110a, 110b with a number of features removed to more clearly see the elasticated waist member 54 and the waist region covering material 101 as well as how the elasticated waist member 54 and the waist region covering material 101 are coupled together and to the body facing surface 19. The described exemplary articles 110a, 110b may be similar to the article 10 of FIG. 2 with respect to the construction of the chassis 11, including the outer cover 24, the absorbent body 34, the bodyside liner 28, the leg cuffs 60, 62, the containment flaps 50, 52, and the fastening system including back fasteners 91 and front fastener 92. Differences between article 10 and articles 110a, 110b concerning the elasticated waist member 54, the waist region covering material 101, and the attachment of the elasticated waist member 54 and the waist region covering material 101 together and to the chassis 11 is described in more detail below.

In the embodiment of FIG. 5, illustrating exemplary absorbent article 110a without adhesive 85 shown and with elasticated waist member 54 shown as transparent to visualize the extent of adhesive 80, the bottom lateral edge 109 of adhesive 80 includes a recessed portion 111. Recessed portion 111 is the portion of the bottom lateral edge 109 of the adhesive 80 that is disposed closer to the rear waist edge 24 than the portion or portions of the bottom lateral edge 109 which are disposed most closely to the crotch region 16. As can be seen, this recessed portion 111 provides an unbonded area 112 where the elasticated waist member 54 is unbonded to the body facing surface 19 of the chassis 11. This unbonded area 112 is a region where the elasticated waist member 54 can flex away from the body facing surface 19 and provide for a containment pocket 82 where body exudates may be captured under the elasticated waist member 54. In general, the recessed portion 111 may have a portion or portions that are disposed most closely to the rear waist edge 24, and this portion that is disposed most closely to the rear waist edge 24 may disposed away from the portion or portions of the bottom lateral edge 109 which are disposed most closely to the crotch region 16 by between 10 mm and 40 mm, or between 15 mm and 30 mm, to provide a sufficiently deep, in the longitudinal direction 30, unbonded area 112 for containing body exudates.

FIGS. 6-8 illustrate exemplary absorbent article 110b providing for an alternative elasticated waist member 54 for providing a containment pocket 82. In various embodiments, the elasticated waist member 54 can include a proximal portion 76 and a distal portion 78. The proximal portion 76, including lateral top edge 61, can be coupled to the body facing surface 19 of chassis 11 (e.g., the body facing surface 45 of the absorbent assembly 44 or the body facing surface 56 of the bodyside liner 28) whereas the distal portion 78, including lateral bottom edge 63, of the elasticated waist member 54 can be free to move with respect to the chassis 11 and the absorbent assembly 44 when the absorbent article 110b is in the relaxed configuration, such as shown in FIG. 7. FIG. 8 provides a cross-sectional view of the elasticated waist member 54 of FIG. 6 depicted in a relaxed configuration, such that the distal portion 78 can be seen extending away from the chassis 11 and absorbent assembly 44 in a vertical direction 33, which is perpendicular to the plane defined by the longitudinal axis 29 and the lateral axis 31. A fold 79 can separate the proximal portion 76 from the distal portion 78. As used in this context, the fold 79 separates the proximal portion 76 from the distal portion 78 in that the fold 79 defines a transition between the proximal portion 76 and the distal portion 78.

The proximal portion 76 of the elasticated waist member 54 can include a longitudinal length measured in the longitudinal direction 30 that is shorter than a longitudinal length of the distal portion 78 of the elasticated waist member 54. However, in some embodiments, the longitudinal length of the proximal portion 76 can be substantially equal to or larger than the longitudinal length of the distal portion 78 of the elasticated waist member 54. For purposes herein, the longitudinal length of the proximal portion 76 and the longitudinal length of the distal portion 78 of the elasticated waist member 54 is measured when the absorbent article 110b is in the stretched, laid flat configuration. It can be appreciated that the relative longitudinal lengths of the proximal portion 76 and the distal portion 78 can be varied between embodiments of the elasticated waist member 54 without departing from the scope of this disclosure.

As illustrated in FIG. 8, because the distal portion 78 of the elasticated waist member 54 can freely move with respect to the absorbent assembly 44 when the absorbent article 10, is in the relaxed configuration, the distal portion 78 can help provide a containment pocket 82 when the absorbent article 110b is in the relaxed configuration. The containment pocket 82 can help provide a barrier to contain and/or can help absorb body exudates. The containment pocket 82 can be especially beneficial for containing and/or absorbing low viscosity fecal matter, which can be prevalent in younger children.

According to some embodiments, the first longitudinal side edge 72 can be disposed laterally outward of the proximal end 64a of the base portion 64 of the containment flap 50, and thus, the pocket 82 can extend laterally outward of the proximal end 64a of the containment flap 50. Similarly, the second longitudinal side edge 74 can be disposed laterally outward of the proximal end 64a of the base portion 64 of the containment flap 52 and the pocket 82 can extend laterally outward of the proximal end 64a of the containment flap 52. Such a configuration provides elasticated waist member 54 with a wide containment pocket 82 to contain and/or absorb body exudates. To help prevent lateral flow of body exudates that are contained by the containment pocket 82 of the elasticated waist member 54, the distal portion 78 of the elasticated waist member 54 can be bonded to the proximal portion 76 of the elasticated waist member 54 and/or the body facing surface 19 of the chassis 11 near the first and second longitudinal side edges 72, 74, respectively. For example, FIGS. 6 & 7 depict tack-down regions 84 where the distal portion 78 of the elasticated waist member 54 can be bonded to the proximal portion 76 of the elasticated waist member 54 and/or the body facing surface 19 of the chassis 11 near the first and second longitudinal side edges 72, 74, respectively.

As described previously, the elasticated waist member 54 can be disposed to be coupled to the chassis 11 by being placed either over the containment flaps 50, 52 or under the containment flaps 50, 52. For example, the elasticated waist member 54 can be disposed on the body facing surface 19 of the chassis 11 such that the proximal portion 76 of the elasticated waist member 54 is disposed over the base portion 64 of the first and the second containment flaps 50, 52, respectively. Alternatively, the elasticated waist member 54 can be disposed on the body facing surface 19 of the chassis 11 such that the proximal portion 76 of the elasticated waist member 54 is disposed under the base portion 64 of the first and the second containment flaps 50, 52, respectively. Both configurations can provide advantages to the functioning of the elasticated waist member 54 according to the present embodiment described with respect to article 110b to contain and/or absorb body exudates.

Embodiments where the proximal portion 76 of the elasticated waist member 54 is disposed over the base portion 64 of the containment flaps 50, 52 can provide the advantage that the containment flaps 50, 52 can help the distal portion 78 of the elasticated waist member 54 extend away from the body facing surface 45 of the absorbent assembly 44 when the absorbent article 110b is applied to the wearer. This is especially relevant where the proximal portion 76 of the elasticated waist member 54 has a shorter longitudinal length than the distal portion 78 of the elasticated waist member 54. For example, in FIGS. 7 & 8, because the proximal portion 76 is shorter than the distal portion 78, the flap elastics 68 in the projection portion 66 of the containment flaps 50, 52 can provide an opening force on the distal portion 78 of the elasticated waist member 54 when the absorbent article 110*b* is in the relaxed configuration and applied to the wearer, thus helping the distal portion 78 extend away from the body facing surface 45 of the absorbent assembly 44 and opening the containment pocket 82. In some embodiments, the containment pocket 82 can be additionally or alternatively opened by configuring the containment flaps 50, 52 to have an active flap elastic region 70 (for example as illustrated in FIG. 2) that longitudinally overlaps with the distal portion 78 of the elasticated waist member 54 when the absorbent article 110*b* is in the stretched, laid flat configuration. Additionally or alternatively, the containment pocket 82 of the elasticated waist member 54 can be opened by configuring the containment flaps 50, 52 to have a tack-down region 71 that does not extend to the free lateral bottom edge 63 of the distal portion 78 of the elasticated waist member 54. However, such a configuration of the tack-down region 71 is not required, and in some embodiments, the tack-down region 71 can extend from the rear waist edge 24 past the free lateral bottom edge 63 of the distal portion 78 of the elasticated waist member 54.

Embodiments where the proximal portion 76 of the elasticated waist member 54 is disposed under the base portion 64 of the containment flaps 50, 52 can provide the advantage of having the containment pocket 82 formed by the elasticated waist member 54 be free from the projection portion 66 of the containment flaps 50, 52. Both the base portion 64 and the projection portion 66 of each containment flap 50, 52 can be coupled to the body facing surface 55 of the elasticated waist member 54. As a result, body exudates may more freely spread through the full width of the containment pocket 82 created by the elasticated waist member 54. Additionally, the coupling of the base portion 64 of the containment flaps 50, 52 to the outer cover 26 (or in some embodiments to the bodyside liner 28) can create a longitudinal barrier to the flow of body exudates out of the containment pocket 82 for exudates that spread laterally beyond the location of the barrier adhesive 49. In some embodiments, the tack-down region 71 of the projection portion 66 of each of the containment flaps 50, 52 can longitudinally overlap with the distal portion 78 of the elasticated waist member 54. In some embodiments, the tack-down region 71 of projection portion 66 of each of the containment flaps 50, 52 can extend to the free lateral bottom edge 63 of the elasticated waist member 54 to further assist in containing exudates within the containment pocket 82 created by the elasticated waist member 54.

Additionally as shown in FIGS. 5-8, the embodiments of articles 110*a* and 110*b* may include a waist region covering material 101. Similar to the embodiments described according to article 10, the waist region covering material 101 may be disposed at least partially over the elasticated waist member 54 of articles 110*a*, 110*b* to provide similar benefits as those described with respect to article 10. Additionally, although the waist region covering material 101 is shown as coupled to the elasticated waist member 54 with adhesives 87*a*, 87*b*, it is contemplated in other embodiments that the connection between the waist region covering material 101 and the elasticated waist member 54 of the embodiments of articles 110*a*, 110*b* may be any suitable connection, including any of the alternative connections as described with respect to article 10 (for example, by adhesive 85 forming a continuous region).

Process 200, with reference to FIG. 9, depicts on exemplary method of manufacturing absorbent article 110*a* described above. Although, it should be evident that process 200 may also be utilized to manufacture other absorbent articles, such as articles 10, 110*b*, with the same process steps. The process 200 may include moving an absorbent assembly 44 in the process direction (PD). The absorbent assembly 44 can be in a discrete form of the chassis 11 for an absorbent article 10, 110*a*, 110*b* as discussed above, or can be in a form of an absorbent assembly web 244 as part of a chassis web 211 comprising a series of interconnected chassis portions 11*a-e*. Although process 200 (and the further processes described herein) illustrates a process whereby rear waist regions of chassis portions lead front waist regions of chassis portions in the process direction PD, it is contemplated that similar processes may be utilized to manufacture the articles 10, 110*a*, 110*b*, 210, and 310 of the present disclosure where the front waist regions of chassis portions lead rear waist regions of chassis portions in the process direction PD.

Typically, such an absorbent assembly 44 (which may be in the form of absorbent assembly web 244) can include a bodyside liner 28 and an outer cover 26, which can be in web form as a bodyside liner web 228 and an outer cover web 226 as well. The absorbent assembly web 244 can include a body facing surface 245. As depicted in FIG. 9, the absorbent assembly web 244 can include multiple distinct chassis portions 11*a-d* which will ultimately be separated into individual articles 110*a*. Separation lines are depicted between each of the chassis portions 11*a-d* which are locations where the absorbent assembly web 244 will be severed, forming discrete articles 110*a*. As noted, the depicted separation line thus becomes a rear waist edge 24 for a trailing chassis portion, such as for chassis portion 11*b*, and a front waist edge 26 for a leading chassis portion, such as for chassis portion 11*a*.

The process 200 can include coupling a pair of containment flaps 250, 252, as are discussed above, and that can each include a base portion 264 and a projection portion 266. The process 200 can also include bonding the base portion 264 of each of the containment flaps 250, 252 to the body facing surface 45 of the absorbent assembly 44 (e.g., the body facing surface 245 of the absorbent assembly web 244). In some embodiments, bonding the base portion 264 of each of the containment flaps 250, 252 to the body facing surface 45 of the absorbent assembly 44 can include bonding the base portion 264 of each of the containment flaps 250, 252 to the bodyside liner 28 (e.g., bodyside liner web 228). In other embodiments, bonding the base portion 264 of each of the containment flaps 250, 252 to the body facing surface 45 of the absorbent assembly 44 can include bonding the base portion 264 of each of the containment flaps 250, 252 to the outer cover 26 (e.g., outer cover web 226). As noted above, the base portion 264 of each of the containment flaps 250, 252 can include a proximal end 364 *a* and a distal end 364 *b*.

The process 200 further includes applying adhesive 80 to the rear waist region 12 of the body facing surface 45 of the absorbent assembly 44, for example as shown with respect to chassis portions 11*a* of the absorbent assembly web 244 where the adhesive 80 is disposed within only a single chassis portion and does not span a separation line. As shown in FIG. 9, the adhesive 80 may be applied with a portion of the lateral bottom edge 63 recessed to provide for formation of a containment pocket once elasticated waist member 54 is adhered to adhesive 80. Although, where other articles—for example, articles 10—may be made by process 200, the adhesive 80 may be applied without a recessed lateral bottom edge 63. Adhesive 80 may be applied according to any suitable method, such as through spraying or slot-coating, or the like. In the embodiment encompassed by FIG. 9, the adhesive 80 may span within only a single chassis portion of the absorbent assembly web 244, for example chassis portion 11b.

Subsequently to adhesive 80 being applied to the body facing surface 245 of the absorbent assembly web 244, an elasticated waist member 54 may be applied to the adhesive 80—for example as shown with respect to chassis portion 11b. Similar to adhesive 80, the elasticated waist member 54 may be disposed within only a single chassis portion and not span a separation line. The elasticated waist member 54 may be applied to adhesive 80 such that the elasticated waist member 54 has a positional relationship with respect to the region defined by the adhesive 80 as described above with respect to the embodiment of article 110a (or articles 10, 110b). Next, an adhesive may further be applied to the elasticated waist member 54, such as is depicted with respect to chassis portion 11c. In the example of FIG. 9, the applied adhesive comprises adhesives 87a, 87b, with an unbonded region disposed between the adhesives 87a, 87, which may be similar to described unbonded region 130. However, it should be understood that other adhesive configurations are possible, particularly a continuous adhesive region as described with respect to some of the embodiments of articles 10, 110a, 110b.

The waist region covering material 101 may then be applied to the elasticated waist member 54. For example chassis 11d is depicted with the waist region covering material 101 applied. The waist region covering material 101 may adhere to both the adhesive disposed on the elasticated waist member 54, adhesives 87a, 87b in the example of FIG. 9, and the adhesive 80 disposed on the body facing surface 45 of the absorbent assembly 44. Similar to the adhesive 80, the waist region covering material 101 may span only a single chassis portion of the absorbent assembly web 244, for example chassis portion 11d, and not span across a separation line. Additionally, the waist region covering material 101 may be applied to the elasticated waist member 54 such that waist region covering material 101 has a positional relationship with respect to the elasticated waist member 54, the adhesive 80, and the body facing surface 245 of the absorbent assembly web 244 (e.g. the body facing surface 45 of the absorbent assembly 44), generally, as described above with respect to any of the embodiment of articles 10, 110a, 110b.

Once the waist region covering material 101 has been applied, the process 200 may further include separating the absorbent assembly web 244 into discrete absorbent articles 110a, as shown in FIG. 9. The severing step includes cutting through only the absorbent assembly web 244 and none of adhesive 80, the elasticated waist member 54, or the waist region covering material 101. The articles 110a may then proceed to be folded and possibly packaged. Such separating, folding, and/or packaging steps may be accomplished according to any generally known process in the art.

FIGS. 10A, 10B depict yet further embodiments of absorbent articles according to aspects of the present disclosure. For example, FIGS. 10A, 10B depict exemplary absorbent article 210 comprising waist region covering material 101 disposed in the rear waist region 14 and a waist region covering material 201 disposed in the front waist region 12.

Articles 210 of FIGS. 10A, 10B may be generally similar to article 10 of FIG. 2 and are additionally depicted with portions of the article 210 absent to more clearly depict the features of interest—as one example, the containment flaps 50, 52. The waist region covering material 201 may, similarly to the waist region covering material 101 described above, help to provide an improved feeling of comfort to a wearer—particularly where the waist region covering material 201 comprises a soft and/or cushiony material. In general, the waist region covering material 201 may comprise any of the optional materials described with respect to waist region covering material 101. In at least some embodiments of article 210, the waist region covering material 101 and the waist region covering material 201 may comprise the same material.

The embodiments of absorbent article 210 may be similar to the embodiments of any of articles 10, 110a, 110b. For example, the article 210 may include a waist containment 54 disposed in the rear waist region and coupled to the body facing surface 45 of the absorbent assembly 44 by adhesive 80. In contrast to the embodiments of articles 10, 110a, 110b, however, the region defined by adhesive 80 of article 210 may comprise a top lateral edge 107 which terminates at the rear waist edge 24. Additionally, the waist region covering material 101 of article 210 disposed may also have its lateral top edge 61 terminate at the rear waist edge 24. According to at least some embodiments of articles 210, the adhesive 80 may be applied with a portion of the lateral bottom edge 63 recessed to provide for formation of a containment pocket once elasticated waist member 54 is adhered to adhesive 80. Although, for clarity purposes, the portion of adhesive 80 covered by the elasticated waist member 54 in FIGS. 10A, 10B is not shown.

Additionally, unlike articles 10, 110a, 110b, the article 210 includes a further waist region covering material 201 disposed in the front waist region 12. The article 210 includes adhesive 81 disposed in the front waist region 12, and the waist region covering material 201 is coupled to the body facing surface 45 of the absorbent assembly 44 by adhesive 81. Adhesive 81 has a first longitudinal side edge 186 and a second longitudinal side edge 188 along with a top lateral edge 185 and a bottom lateral edge 189, with the top lateral edge 185 being disposed closer to the crotch region 16 than the bottom lateral edge 189. The waist region covering material 201 comprises first longitudinal side edge 202, second longitudinal side edge 204, top lateral edge 203, and bottom lateral edge 205, with top lateral edge 203 disposed closer to the crotch region 16 than the bottom lateral edge 205.

As illustrated in FIG. 10A, the edges 186, 188, and 185 are generally spaced from the edges 202, 204, and 203 of the waist region covering material 201 such that the waist region covering material 201 fully covers the region of adhesive 81. The edges 189 and 205 may both terminate at the front waist edge 22. Although, in some embodiments, the top lateral edge 185 and the top lateral edge 203 may overlap in the vertical direction 33 such that the edges 185, 203 are disposed at approximately the same distance from the crotch region 16. It may be generally undesirable to leave the region of adhesive 81 uncovered by the waist region covering material 201 and, or another material layer, as the uncovered adhesive 81 may cause the article 210 to stick together in a folded state and/or cause tearing of one or more of the layers of the article 210 when the article 210 is unfolded.

Of course, providing for a continuous region of adhesive 81 is not the only way that the waist region covering material 201 may be coupled to the body facing surface 45 of the absorbent assembly 44 of article 210. For example, as illustrated in FIG. 10B, the waist region covering material 201 may be coupled to the body facing surface 45 of the absorbent assembly 44 by at least a first connection and a second connection, such as by adhesives 187a, 187b. In such embodiments, the article 210 of FIG. 10B need not have the top lateral edge 107 of adhesive 80 extend all the way to the rear waist edge 24. Rather, in at least some of these embodiments, top lateral edge 107 of adhesive 80 is spaced from the rear waist edge 24, as is shown in FIG. 10B.

The adhesives 187a, 187b may be lines or stripes of adhesives with adhesive 187a disposed proximate the bottom lateral edge 205 of the waist region covering material 201 and the adhesive 187b disposed proximate the top lateral edge 203. The adhesives 187a, 187b may generally be similar to the adhesives 87a, 87b described previously—for example having similar longitudinal lengths extending in the longitudinal direction 30. Additionally, the adhesives 187a, 187b may be spaced similar distances from the lateral bottom edge 205 and lateral top edge 203 as described for the adhesives 87a, 87b with respect to edges 63, 61 of article elasticated waist member 54. Further embodiments of article 210 are contemplated which include connections in addition to adhesives 187a, 187b—for example, one, two, three, four, or more additional connections, such as additional lines or regions of adhesive.

Additionally, the disposition of the adhesives 187a, 187b, and any other connections connecting the waist region covering material 201 to the front waist region 12 of the article 210, may be chosen such that there is an unbonded region 132 where the waist region covering material 201 is uncoupled to the body facing surface 45 of the absorbent assembly 44. Such an unbonded region 132 may provide a benefit of allowing the waist region covering material 201 to flex away from the assembly 44, providing for an increased feeling of softness by a wearer, particularly where the waist region covering material 201 is softer and/or more flexible than the body facing surface 45 of the absorbent assembly 44 in the front waist region 12. According to aspects of the present disclosure, a longitudinal length of the unbonded region 132 may generally be desired to be greater than 10 mm. In other embodiments, the unbonded region 132 may be greater than 15 mm, or greater than 20 mm, or greater than 25 mm, or greater than 30 mm, or greater than 35 mm, or greater than 40 mm, or greater than 50 mm. The unbonded region 132 may generally be less than 75 mm or less than 65 mm in any of the above embodiments.

FIG. 11 depicts an exemplary process 200' for manufacturing absorbent articles 210, as described above. Process 200' may be substantially similar to the previously described process 200. For example, the process 200' may include similar steps of moving an absorbent assembly 44 in the process direction (PD), which can be in a form of an absorbent assembly web 244 as part of a chassis web 211 comprising a series of interconnected chassis 11a-d. Process 200' may similarly including coupling containment flaps 250, 252 to the body facing surface 45 of the absorbent assembly 44 (e.g., the body facing surface 245 of the absorbent assembly web 244).

One difference of process 200' however is in the application of adhesive 80 to the absorbent assembly web 244. As shown in FIG. 11, the process 200' comprises applying adhesive 80 to the rear waist region 14 of chassis portion 11a and to the front waist region 12 of chassis 11b. Like the process 200, the process 200' can, but does not need to, include applying adhesive 80 in the rear waist region 14 of a chassis portion with a lateral bottom edge 63 having a recessed portion. In general, the adhesive 80 may be applied by a single adhesive applicator while spanning between chassis portions 11a, 11b. As the adhesive 80 is applied to both the rear waist region 14 and the front waist region 12 of successive chassis portions 11a, 11b, in the process direction PD, the adhesive 80 thus spans the depicted separation line between chassis portions 11a, 11b, which becomes the rear waist edge 24 for chassis portion 11a and the front waist edge 22 for chassis portion 11b. For this reason, in the embodiments of articles 210, the adhesive 80 may terminate at both the rear waist edge 24 and the front waist edge 22, instead of being spaced from edges 24, 22 as described with respect to other embodiments according to the present disclosure.

After adhesive 80 is applied to the absorbent assembly web 244 and spanning between a rear waist region 14 of a first chassis portion and a front waist region 12 of a second chassis portion, for example chassis portions 11a, 11b, the elasticated waist member 54 may be applied to the adhesive 80 in the rear waist region 14, similar to process 200. Process 200' may further include applying adhesives 87a, 87b to the elasticated waist member 54, as in process 200, for example as shown with respect to chassis portion 11c. Although, in other contemplated embodiments, an adhesive forming a continuous region, such as adhesive 85 as shown in FIGS. 3A, 4A, may be applied to the elasticated waist member 54.

Another difference between process 200 and process 200', is in the coupling of the waist region covering material 101 to the absorbent assembly web 244. In the embodiment of process 200', the waist region covering material 101 is coupled to the absorbent assembly web 244 in both the rear waist region 14 of a first chassis portion, such as chassis portion 11d, and a front waist region 12 of a second chassis portion, such as chassis portion 11e. As can be seen, the waist region covering material 101 spans the separation line depicted between the chassis portions 11d, 11e. Accordingly, the waist region covering material 101 may be coupled to both the rear waist region 14 of the first chassis portion 11d and the front waist region 12 of the second chassis portion 11e through adhesive 80 (as well as to the elasticated waist member 54 such as through adhesives 87a, 87b).

One alternative embodiment of process 200' is where the adhesive 80 is applied only to the rear waist region 14 of a first chassis portion, such as chassis portion 11a—similar to how adhesive 80 is applied in process 200. In order to secure the waist region covering material 101 to the front waist region 12 of a chassis portion of the absorbent assembly web 244, additional adhesive applications may be applied to the front waist region 12, such as adhesives 187a, 187b. Adhesives 187a, 187b were described with respect to embodiments of absorbent articles 210 depicted in FIG. 10B. In such an alternative process 200', the adhesives 187a, 187b may be applied in conjunction with application of adhesives 87a, 87b, for example by the same adhesive applicator. For example, after the adhesive 80 is applied only to the rear waist region 14 of a first chassis portion, such as chassis portion 11a, the elasticated waist member 54 may be applied to the adhesive 80. Subsequently, an adhesive applicator may apply adhesives 187a, 187b to a front waist region 12 of a first chassis portion, for example chassis portion 11d, and adhesives 87a, 87b to elasticated waist member 54 in the rear waist region 14 of a second chassis portion, such as chassis portion 11c.

Once the adhesives 187a, 187b, 87a, and 87b have been applied to the front waist region 12 of the first chassis portion and the elasticated waist member 54 in the rear waist region 14 of the second chassis portion, the waist region covering material 101 may be coupled both of the front waist region 12 of the first chassis portion and the elasticated waist member 54 in the rear waist region 14, for example as shown with respect to chassis portions 11d, 11e. Similar to adhesive 80, the waist region covering material 101, 201 of articles 210 having edges 103, 205 which terminate at the front and rear waist edges 22, 24 rather than be spaced from the waist edges 22, 24 is because the waist region covering material 101 spans the separation line between successive chassis portions and which becomes the front and rear waist edges 22, 24 of successive articles 210 in the process direction PD.

Once the waist region covering material 101 has been applied, the process 200' may further include separating the absorbent assembly web 244 into discrete absorbent articles 210, as shown in FIG. 11. The severing step includes cutting through only the absorbent assembly web 244, including adhesive 80 and the waist region covering material 101, but not the elasticated waist member 54. At this point, the waist region covering material 101 has been separated into discrete pieces, with a first piece attached to a rear waist region 14, for example with respect to chassis portion 11e which will become a discrete article 210, and with the second piece attached to the front waist region 12, for example article 210 of FIG. 11. The second piece becomes waist region covering material 201 upon this separation with the first piece of the waist region covering material 101. Finally, the articles 210 may then proceed to be folded and possibly packaged. Such separating, folding, and/or packaging steps may be accomplished according to any generally known process in the art.

FIGS. 12A, 12B depict yet further exemplary embodiments of absorbent articles according to aspects of the present disclosure. For example, FIGS. 12A, 12B depict exemplary absorbent article 310 comprising a first elasticated waist member 54 disposed in the rear waist region 14 and a second elasticated waist member 54 disposed in the front waist region 12. Articles 310 of FIGS. 12A, 12B may be generally similar to article 10 of FIG. 2 and are additionally depicted with portions of the article 310 absent to more clearly depict the features of interest—as one example, the containment flaps 50, 52. Additionally, similar to articles 210, embodiments according to article 310 may have a waist region covering material 101 disposed in the rear waist region 14 and a waist region covering material 201 disposed in the front waist region 12. Accordingly, in the embodiments of FIGS. 12A, 12B, article 310 may have the waist region covering material 201 coupled to the body facing surface 45 of the absorbent assembly 44 in the front waist region 12 and coupled to at least a portion of the second elasticated waist member 54 disposed in the front waist region 12.

The embodiments of absorbent article 310 may be similar to the embodiments of any of articles 10, 110a, 110b, and particularly to the embodiment of article 210. For example, the article 310 may include an elasticated waist member 54 disposed in the rear waist region 14 and coupled to the body facing surface 45 of the absorbent assembly 44 by adhesive 80. In contrast to the embodiments of articles 10, 110a, 110b, and similar to the embodiment of article 210, the region defined by adhesive 80 of article 310 may comprise a top lateral edge 107 which terminates at the rear waist edge 24. Additionally, the waist region covering material 101 of article 310 may be disposed to also have its lateral top edge 61 terminate at the rear waist edge 24. According to at least some embodiments of article 310, the adhesive 80 may be applied with a portion of the lateral bottom edge 63 recessed to provide for formation of a containment pocket once elasticated waist member 54 is adhered to adhesive 80.

Article 310 may include adhesive 81 disposed in the front waist region 12, similar to article 210. For example, adhesive 81 is shown as having a first and second longitudinal side edges 186, 188 as well as top and bottom lateral edges 185, 189. The top lateral edge 185 is disposed closer to the crotch region 16 than the bottom lateral edge 189. The second elasticated waist member 54 of article 310 is coupled to adhesive 81 to secure the second elasticated waist member 54 to the body facing surface 45 of the absorbent assembly 44. Although shown generally as covering a rectangular region, the adhesive 81 may be formed to have the top lateral edge 185 recessed toward the front waist edge 22 to form a containment pocket—for example in a similar fashion as described with respect to adhesive 80 in the rear waist region 14 of article 110a of FIG. 5. The second elasticated waist member 54 is shown as having a lateral top edge 261, a lateral bottom edge 263, and first and second longitudinal side edges 272 and 274.

Like articles 210, the article 310 further includes waist region covering material 201 disposed in the front waist region 12 and coupled to the body facing surface 45 of the absorbent assembly 44 at least partially by adhesive 81. The waist region covering material 201 comprises first and second longitudinal side edges 202, 204, top lateral edge 203, and bottom lateral edge 205. The top lateral edge 203 is disposed closer to the crotch region 16 than the bottom lateral edge 205. Additionally, the top lateral edge 203 of the waist region covering material 201 may be disposed closer to the crotch region 16 than the lateral top edge 261 of the second elasticated waist member 54. In other embodiments, the top lateral edge 203 may be disposed at approximately the same position as the lateral top edge 261 such that the top lateral edge 203 and the lateral top edge 261 overlap in the vertical direction 33.

As illustrated in FIG. 12A, the edges 186, 188, and 185 are generally spaced from the edges 202, 204, and 203 of the waist region covering material 201 such that the waist region covering material 201 fully covers the region of adhesive 81. The edges 189 and 205 may both terminate at the front waist edge 22. Although, in some embodiments, the top lateral edge 185 and the top lateral edge 203 may overlap in the vertical direction 33 such that the edges 185, 203 are disposed at approximately the same distance from the crotch region 16. It may be generally undesirable to leave the region of adhesive 85 uncovered by the waist region covering material 201 and, or another material layer.

The waist region covering material 201 is further coupled to the second elasticated waist member 54 at least partially through adhesive 285, as shown in FIG. 12A. For example, prior to application of the waist region covering material 201, adhesive 285 may be applied to the second elasticated waist member 54. As shown, a region bounded by adhesive 285 may have top, bottom, and longitudinal side edges—although these edges are not specifically labeled. Such edges may be generally spaced inward from corresponding lateral top and longitudinal side edges 261, 272, and 274 of the second elasticated waist member 54. Although, this may not necessarily be the case in all embodiments. For example, in some embodiments, a top lateral edge of the region bounded by adhesive 285 may overlap in the vertical direction 33 with lateral top edge 261. Although, it may be important for a top lateral edge of the region bounded by adhesive 285 to not extend closer to the crotch region 16 than the lateral top edge 261 of the second elasticated waist member 54 (or the waist region covering material 201 where the waist region covering material 201 extends closer to the crotch region 16 than the second elasticated waist member 54).

Of course, providing for a continuous region of adhesive 285 is not the only way that the waist region covering material 201 may be coupled to the second elasticated waist member 54. For example, as illustrated in FIG. 12B, the waist region covering material 201 may be coupled to the second elasticated waist member 54 by at least a first connection and a second connection, such as by adhesives 187a, 187b. The adhesives 187a, 187b may be lines or stripes of adhesives with adhesive 187a disposed proximate lateral bottom edge 263 of the second elasticated waist member 54 and the adhesive 187b disposed proximate lateral top edge 261 of the second elasticated waist member 54. The adhesives 187a, 187b may generally be similar to the adhesives 87a, 87b described previously with respect to embodiments of article 10—for example having similar longitudinal lengths extending in the longitudinal direction 30. Additionally, the adhesives 187a, 187b may be spaced similar distances from the lateral bottom edge 263 and lateral top edge 261 as described for the adhesives 87a, 87b with respect to edges 63, 61 of the elasticated waist member 54 of article 10. Further embodiments of article 310 are contemplated which include connections in addition to adhesives 187a, 187b—for example, one, two, three, four, or more additional connections, such as additional lines or regions of adhesive.

Additionally, the disposition of the adhesives 187a, 187b, and any other connections connecting the waist region covering material 201 to the second elasticated waist member 54, may be chosen such that there is an unbonded region 232 where the waist region covering material 201 is uncoupled to the second elasticated waist member 54. Such an unbonded region 232 may provide a benefit of allowing the waist region covering material 201 to flex away from the second elasticated waist member 54, providing for an increased feeling of softness by a wearer, particularly where the waist region covering material 201 is softer and/or more flexible than the second elasticated waist member 54. According to aspects of the present disclosure, a longitudinal length of the unbonded region 232 may generally be desired to be greater than 10 mm. In other embodiments, the unbonded region 232 may be greater than 15 mm, or greater than 20 mm, or greater than 25 mm, or greater than 30 mm, or greater than 35 mm, or greater than 40 mm, or greater than 50 mm. The unbonded region 232 may generally be less than 75 mm or less than 65 mm in any of the above embodiments.

FIG. 13 depicts an exemplary process 200" for manufacturing absorbent articles 310, as described above. Process 200" may be substantially similar to the previously described process 200. For example, the process 200" may include similar steps of moving an absorbent assembly 44 in the process direction (PD), which can be in a form of an absorbent assembly web 244 as part of a chassis web 211 comprising a series of interconnected chassis 11a-e. Process 200" may similarly including coupling containment flaps 250, 252 to the body facing surface 45 of the absorbent assembly 44 (e.g., the body facing surface 245 of the absorbent assembly web 244).

One difference of process 200" however is in the additional application of a second elasticated waist member 54 disposed in the front waist region 12 of the chassis portions, such as is shown with respect to chassis portion 11b. Application of the second elasticated waist member 54 may be at close in time to the application of the first elasticated waist member 54 disposed in the rear waist region 14, for example as shown with respect to chassis portion 11b of the absorbent assembly web 244. The first elasticated waist member 54 and the second elasticated waist member 54 may be applied by a same elasticated waist member application module or by separate elasticated waist member application modules disposed in series. As with the first elasticated waist member 54 disposed in the rear waist region 14, the second elasticated waist member 54 is applied after application of adhesive 80.

Following application of both the first elasticated waist member 54 and the second elasticated waist member 54, process 200" includes applying adhesive to both of the first elasticated waist member 54 and the second elasticated waist member 54. For example, as shown in FIG. 13, adhesives 87a, 87b may be applied to the first elasticated waist member 54 disposed in the rear waist region 14 of chassis portion 11c. Adhesives 187a, 187b may additionally be applied to the second elasticated waist member 54 disposed in the front waist region 12 of chassis portion 11c. However, in other contemplated embodiments, an adhesive forming a continuous region, such as adhesive 85 as shown in FIGS. 3A, 4A, may be applied to either, or both of, the first elasticated waist member 54 and the second elasticated waist member in place of adhesives 87a, 87b and/or 187a, 187b.

The process 200" may further comprise, similar to process 200', coupling of the waist region covering material 101 to the absorbent assembly web 244. As in process 200', the process 200" includes applying the waist region covering material 101 to the absorbent assembly web 244 in both the rear waist region 14 of a first chassis portion, such as chassis portion 11d, and a front waist region 12 of a second chassis portion, such as chassis portion 11e. More specifically, in the embodiment of FIG. 13, process 200" includes coupling the waist region covering material 101 to adhesive 80 and the first elasticated waist member 54 (through adhesives 87a, 87b) in the rear waist region 14 of the chassis portion 11d and adhesive 80 and the second elasticated waist member 54 (through adhesives 187a, 187b) in the front waist region 12 of the chassis portion 11e.

As shown in the primary embodiment of FIG. 13, the waist region covering material 101 may span the separation line depicted between the chassis portions 11d, 11e. Once the waist region covering material 101 has been applied, the process 200" may further include separating the absorbent assembly web 244 into discrete absorbent articles 310, as shown in FIG. 13. The severing step includes cutting through the absorbent assembly web 244 including adhesive 80 and the waist region covering material 101 at a location disposed between the first elasticated waist member 54 and the second elasticated waist member 54, for example as can be seen with respect to article 310 and chassis portion 11e. At this point, the waist region covering material 101 has been separated into discrete pieces, with a first piece attached to a rear waist region 14 and with a second piece attached to the front waist region 12. The second piece becomes the waist region covering material 102 upon this separation with the first piece of the waist region covering material 101.

As can be seen, the waist region covering material 101, 201 having edges 103, 205 which terminate at the front and rear waist edges 22, 24 rather than be spaced from the waist edges 22, 24 because the waist region covering material 101 spanned the separation line between successive chassis portions and which becomes the front and rear waist edges 22, 24 of successive articles 310 in the process direction PD. Finally, the articles 310 may then proceed to be folded and possibly packaged. Such separating, folding, and/or packaging steps may be accomplished according to any generally known process in the art.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

EMBODIMENTS

Embodiment 1: An absorbent article including a front waist region including a front waist edge, a rear waist region including a rear waist edge, a crotch region disposed between the front waist region and the rear waist region, a longitudinal axis extending in a longitudinal direction and a lateral axis extending in a lateral direction, the absorbent article comprising a chassis including an absorbent body, the chassis including a body facing surface; a first adhesive disposed on the body facing surface of the chassis; an elasticated waist member coupled to the body facing surface of the chassis by the first adhesive; a second adhesive disposed on the elasticated waist member; and a waist region covering material coupled to the elasticated waist member by the second adhesive.

Embodiment 2: The absorbent article of embodiment 1, wherein a portion of the waist region covering material may extend beyond a boundary of the elasticated waist member, the portion of the waist region covering material extending beyond a boundary of the elasticated waist member being coupled to the body facing surface of the chassis by the first adhesive.

Embodiment 3: The absorbent article of embodiment 1 or 2, wherein at least some of the second adhesive may be disposed directly on the first adhesive.

Embodiment 4: The absorbent article of any one of embodiments 1-3, wherein the second adhesive may comprise at least two adhesive regions spaced apart in the longitudinal direction.

Embodiment 5: The absorbent article of embodiment 4, further comprising an unbonded region where the waist region covering material is uncoupled to the elasticated waist member disposed between the at least two adhesive regions, the unbonded region may have a length in the longitudinal direction of greater than 10 mm.

Embodiment 6: The absorbent article of embodiment 5, wherein the unbonded region may have a length in the longitudinal direction of greater than 20 mm.

Embodiment 7: The absorbent article of any one of embodiments 4-6, wherein each of the at least two adhesive regions have lengths in the longitudinal direction of less than 10 mm.

Embodiment 8: The absorbent article of any one of embodiments 1-7, wherein the waist region covering material has a lateral top edge and a lateral bottom edge, the lateral top edge being disposed closer to the rear waist edge than the lateral bottom edge, and wherein the lateral top edge may be spaced from the rear waist edge by greater than 3 mm.

Embodiment 9: The absorbent article of any one of embodiments 1-8, wherein the waist region covering material has a lateral top edge and a lateral bottom edge, the lateral top edge being disposed closer to the rear waist edge than the lateral bottom edge, and wherein the lateral top edge may be disposed at approximately the same longitudinal position as the rear waist edge such that the lateral top edge and the rear waist edge overlap in a vertical direction perpendicular to the longitudinal direction and the lateral direction.

Embodiment 10: The absorbent article of any one of embodiments 1-9, wherein the waist region covering material has a lateral top edge and a lateral bottom edge with the lateral top edge being disposed closer to the rear waist edge than the lateral bottom edge, the elasticated waist member has a top lateral edge and a bottom lateral edge with the top lateral edge being disposed closer to the rear waist edge than the bottom lateral edge, and wherein the lateral bottom edge of the waist region covering material may be disposed closer to the crotch region than the bottom lateral edge of the elasticated waist member.

Embodiment 11: The absorbent article of any one of embodiments 1-10, wherein the waist region covering material has a lateral top edge and a lateral bottom edge with the lateral top edge being disposed closer to the rear waist edge than the lateral bottom edge, the elasticated waist member has a top lateral edge and a bottom lateral edge with the top lateral edge being disposed closer to the rear waist edge than the bottom lateral edge, and wherein the bottom lateral edge of the elasticated waist member may be disposed closer to the crotch region than the lateral bottom edge of the waist region covering material.

Embodiment 12: The absorbent article of any one of embodiments 1-11, wherein the first adhesive has a top lateral edge and a bottom lateral edge with the top lateral edge being disposed closer to the rear waist edge than the bottom lateral edge, the bottom lateral edge optionally further comprising a recessed portion that is disposed closer to the top lateral edge than other, non-recessed portions of the bottom lateral edge.

Embodiment 13: An absorbent article including a front waist region including a front waist edge, a rear waist region including a rear waist edge, a crotch region disposed between the front waist region and the rear waist region, a longitudinal axis extending in a longitudinal direction and a lateral axis extending in a lateral direction, the absorbent article comprising: a chassis including an absorbent body, the chassis including a body facing surface; a first adhesive disposed on the body facing surface of the chassis in the rear waist region; an elasticated waist member coupled to the body facing surface of the chassis in the rear waist region by the first adhesive; a first waist region covering material coupled to the body facing surface of the chassis and disposed entirely in the rear waist region, the first waist region covering material covering at least a portion of the elasticated waist member and having a lateral top edge and a lateral bottom edge, the lateral top edge being disposed closer to the rear waist edge than the lateral bottom edge; and a second waist region covering material coupled to the body facing surface of the chassis and disposed entirely in the front waist region and having a lateral top edge and a lateral bottom edge, the lateral top edge being disposed closer to the crotch region than the lateral bottom edge, the first waist region covering material and the second waist region covering material being formed of a same material. The lateral top edge of the first waist region covering material may be disposed at approximately the same longitudinal position as the rear waist edge such that the lateral top edge and the rear waist edge overlap in a vertical direction perpendicular to the longitudinal direction and the lateral direction, and the lateral bottom edge of the second waist region covering material may be disposed at approximately the same longitudinal position as the front waist edge such that the lateral bottom edge and the front waist edge overlap in the vertical.

Embodiment 14: The absorbent article of embodiment 13, wherein the second waist region covering material may be coupled to the body facing surface of the chassis by a second adhesive, wherein the first adhesive and the second adhesive comprise a same adhesive.

Embodiment 15: The absorbent article of embodiment 14, wherein the first adhesive and the second adhesive may be applied by a same adhesive applicator.

Embodiment 16: The absorbent article of any one of embodiments 13-15, further comprising a third adhesive disposed on the elasticated waist member, the first waist region covering material coupled to the elasticated waist member by the third adhesive.

Embodiment 17: The absorbent article of embodiment 16, wherein the third adhesive may comprise at least two adhesive regions spaced apart in the longitudinal direction.

Embodiment 18: The absorbent article of embodiment 17, further comprising an unbonded region where the waist region covering material is uncoupled to the elasticated waist member disposed between the at least two adhesive regions, the unbonded region having a length in the longitudinal direction of greater than 10 mm.

Embodiment 19: The absorbent article of embodiment 18, wherein the unbonded region may have a length in the longitudinal direction of greater than 20 mm.

Embodiment 20: The absorbent article of any one of embodiments 13-19, further comprising a second adhesive disposed in the front waist region and an elasticated waist member coupled to the body facing surface of the chassis in the front waist region by the second adhesive, wherein the second waist region covering material may at least partially covers the elasticated waist member coupled to the body facing surface of the chassis in the front waist region.

Embodiment 21: The absorbent article of embodiment 20, further comprising a fourth adhesive disposed on the elasticated waist member coupled to the body facing surface of the chassis in the front waist region, and wherein the second waist region covering material may be coupled to the elasticated waist member coupled to the body facing surface of the chassis in the front waist region by the fourth adhesive.

Embodiment 22: The absorbent article of embodiment 21, wherein the fourth adhesive may comprise at least two adhesive regions spaced apart in the longitudinal direction.

Embodiment 23: The absorbent article of embodiment 22, further comprising an unbonded region where the waist region covering material is uncoupled to the elasticated waist member disposed between the at least two adhesive regions, the unbonded region may optionally having a length in the longitudinal direction of greater than 10 mm.

Embodiment 24: The absorbent article of embodiment 23, wherein the unbonded region may have a length in the longitudinal direction of greater than 20 mm.

Embodiment 25: The absorbent article of any one of embodiments 13-24, wherein the first adhesive has a top lateral edge and a bottom lateral edge, the top lateral edge being disposed closer to the rear waist edge than the bottom lateral edge, and wherein the top lateral edge may be disposed at approximately the same longitudinal position as the rear waist edge such that the top lateral edge and the rear waist edge overlap in the vertical direction.

Embodiment 26: The absorbent article of any one of embodiments 14-25, wherein the second adhesive has a top lateral edge and a bottom lateral edge, the bottom lateral edge being disposed closer to the front waist edge than the top lateral edge, and wherein the bottom lateral edge may be disposed at approximately the same longitudinal position as the front waist edge such that the bottom lateral edge and the front waist edge overlap in the vertical direction.

Embodiment 27: The absorbent article of any one of embodiments 13-26, wherein the first adhesive has a top lateral edge and a bottom lateral edge, the top lateral edge being disposed closer to the rear waist edge than the bottom lateral edge, and the bottom lateral edge may comprise a recessed portion that is disposed closer to the top lateral edge than other, non-recessed portions of the bottom lateral edge.

Embodiment 28: The absorbent article of any one of embodiments 14-27, wherein the second adhesive has a top lateral edge and a bottom lateral edge, the bottom lateral edge being disposed closer to the front waist edge than the top lateral edge, and the top lateral edge may comprise a recessed portion that is disposed closer to the bottom lateral edge than other, non-recessed portions of the top lateral edge.

Embodiment 29: A method of forming absorbent articles comprising: moving a chassis web in a machine direction, the chassis web comprising an outer cover, an absorbent body, and a chassis web body facing surface; applying a first adhesive to the chassis web body facing surface, the first adhesive defining a first adhesive region; coupling an elasticated waist member to the chassis web with the first adhesive; applying a second adhesive to the elasticated waist member; coupling a waist region covering material to the elasticated waist member with the second adhesive; severing the chassis web to form an individual absorbent article, the severing step comprises cutting through a portion of the chassis web comprising the first adhesive and the waist region covering material but not the elasticated waist member.

Embodiment 30: The method of embodiment 29, wherein the elasticated waist member may be applied to the chassis web such that the elasticated waist member covers only part of the first adhesive such that a portion of the first adhesive is left uncovered by the elasticated waist member.

Embodiment 31: The method of embodiment 29 or 30, wherein the applied first adhesive may have a bottom lateral edge and a top lateral edge with the bottom lateral edge comprising a recessed portion that is disposed closer to the top lateral edge than other, non-recessed portions of the bottom lateral edge.

Embodiment 32: The method of any one of embodiments 29-31, wherein the second adhesive may comprise at least two adhesive regions spaced apart in the machine direction.

Embodiment 33: The method of embodiment 32, further comprising an unbonded region where the waist region covering material may be uncoupled to the elasticated waist member disposed between the at least two adhesive regions, the unbonded region having a length in the machine direction of greater than 10 mm.

Embodiment 34: The method of embodiment 33, wherein the unbonded region may have a length in the longitudinal direction of greater than 20 mm.

Embodiment 35: The method of any one of embodiments 29-34, wherein the chassis web may comprise a series of separation lines where the chassis web is severed to form individual absorbent articles, and wherein severing the chassis web at a first separation line may form a front waist edge of a first absorbent article separated from the chassis web and a resulting leading edge of the chassis web forms a rear waist edge of a second absorbent article, the second absorbent article separated from the chassis web by severing the chassis web at a second separation line, the second separation line trailing the first separation line in the machine direction.

Embodiment 36: The method of embodiment 35, wherein applying the first adhesive to the chassis web body facing surface may comprise applying the first adhesive such that it crosses a separation line.

Embodiment 37: The method of embodiment 35 or 36, wherein coupling the waist region covering material to the elasticated waist member with the second adhesive may further comprise coupling the waist region covering material to a portion the first adhesive, wherein the elasticated waist member may be disposed on a trailing portion of the chassis web in relation to an adjacent separation line and wherein at least part of the portion of the first adhesive coupled to the waist region covering material may be disposed on a leading portion of the chassis web relative to the adjacent separation line.

Embodiment 38: The method of embodiment 36 or 37, wherein coupling the elasticated waist member to the chassis web with the first adhesive may comprise coupling a first elasticated waist member to the first adhesive on a trailing portion of the chassis web in relation to an adjacent separation line, and may further comprise coupling a second elasticated waist member to the chassis web with the first adhesive on a leading portion of the chassis web in relation to the adjacent separation line.

Embodiment 39: The method of embodiment 38, further comprising applying a third adhesive to the second elasticated waist member and coupling the waist region covering material to the third adhesive.

Embodiment 40: The method of embodiment 39, wherein the third adhesive may comprise at least two adhesive regions spaced apart in the machine direction.

Embodiment 41: The method of embodiment 40, further comprising an unbonded region where the waist region covering material may be uncoupled to the second elasticated waist member disposed between the at least two adhesive regions, the unbonded region having a length in the machine direction of greater than 10 mm.

Embodiment 42: The method of embodiment 41, wherein the unbonded region may have a length in the longitudinal direction of greater than 20 mm.

Embodiment 43: The method of any one of embodiments 38-42, wherein the step of severing the chassis web to form an individual absorbent article may comprise cutting through a portion of the chassis web comprising the first adhesive and the waist region covering material and disposed between the first elasticated waist member and the second elasticated waist member.

Embodiment 44: The method of any one of embodiments 29-43, further comprising folding the separated individual absorbent article.

What is claimed is:

1. An absorbent article including a front waist region including a front waist edge, a rear waist region including a rear waist edge, a crotch region disposed between the front waist region and the rear waist region, a longitudinal axis extending in a longitudinal direction and a lateral axis extending in a lateral direction, the absorbent article comprising:

a chassis including an absorbent body, the chassis including a body facing surface;

a first adhesive disposed on the body facing surface of the chassis;

an elasticated waist member coupled to the body facing surface of the chassis by the first adhesive, the elasticated waist member comprising a plurality of elastic strands spaced apart in the longitudinal direction, the plurality of elastic strands enclosed by a first non-woven material;

a second adhesive disposed on the elasticated waist member; and a waist region covering material coupled to the elasticated waist member by the second adhesive, the waist region covering material comprising a second non-woven material, different from the first non-woven material and having a loft that is greater than 1.0 mm, wherein the first adhesive extends beyond a boundary of the elasticated waist containment member, and wherein a portion of the waist region covering material also extends beyond the boundary of the elasticated waist member, the portion of the waist region covering material extending beyond the boundary of the elasticated waist member being coupled to the body facing surface of the chassis by the first adhesive.

2. The absorbent article of claim 1, wherein at least some of the second adhesive is disposed directly on the first adhesive.

3. The absorbent article of claim 1, wherein the second adhesive comprises at least two adhesive regions spaced apart in the longitudinal direction.

4. The absorbent article of claim 3, further comprising an unbonded region where the waist region covering material is uncoupled to the elasticated waist member disposed between the at least two adhesive regions, the unbonded region having a length in the longitudinal direction of greater than 10 mm.

5. The absorbent article of claim 4, wherein the unbonded region has a length in the longitudinal direction of greater than 20 mm.

6. The absorbent article of claim 3, wherein each of the at least two adhesive regions have lengths in the longitudinal direction of less than 10 mm.

7. The absorbent article of claim 1, wherein the waist region covering material has a lateral top edge and a lateral bottom edge, the lateral top edge being disposed closer to the rear waist edge than the lateral bottom edge, and wherein the lateral top edge is spaced from the rear waist edge by greater than 3 mm.

8. The absorbent article of claim 1, wherein the waist region covering material is a TABCW material.

9. The absorbent article of claim 8, wherein the waist region covering material has a basis weight of between 10 gsm and 50 gsm.

10. The absorbent article of claim 1, wherein the waist region covering material has a loft of greater than 1.5 mm.

* * * * *